(12) United States Patent
Rho et al.

(10) Patent No.: US 9,326,968 B2
(45) Date of Patent: May 3, 2016

(54) COMPOSITION FOR ENHANCING IMMUNITY CONTAINING COMPOUNDS REPRESENTED BY CHEMICAL FORMULAS 1-8 OR SOPHORA FLAVESCENS EXTRACT AS ACTIVE INGREDIENT

(75) Inventors: Mun Chual Rho, Daejeon (KR); Woo Song Lee, Daejeon (KR); Kyoung Oh Cho, Daejeon (KR); Su Jin Park, Daejeon (KR); Young Bae Ryu, Daejeon (KR); Young Min Kim, Daejeon (KR); Seung Woong Lee, Daejeon (KR); Ji Hak Jeong, Daejeon (KR); Mi Hye Park, Daejeon (KR); Jong Sun Chang, Daejeon (KR)

(73) Assignee: Korea Research Institute of Bioscience and Biotechnology, Daejeon (KR)

( * ) Notice: Subject to any disclaimer, the term of this patent is extended or adjusted under 35 U.S.C. 154(b) by 201 days.

(21) Appl. No.: 13/876,437

(22) PCT Filed: Mar. 28, 2011

(86) PCT No.: PCT/KR2011/002120
§ 371 (c)(1),
(2), (4) Date: Jun. 10, 2013

(87) PCT Pub. No.: WO2012/043949
PCT Pub. Date: Apr. 5, 2012

(65) Prior Publication Data
US 2013/0303474 A1    Nov. 14, 2013

(30) Foreign Application Priority Data
Sep. 27, 2010    (KR) .......................... 10-2010-0093423

(51) Int. Cl.
  *A61K 31/353*    (2006.01)
  *A61K 31/704*    (2006.01)
  *A61K 31/35*    (2006.01)

(52) U.S. Cl.
  CPC .............. *A61K 31/353* (2013.01); *A61K 31/35* (2013.01); *A61K 31/704* (2013.01)

(58) Field of Classification Search
  CPC .... A61K 31/35; A61K 31/353; A61K 31/704
  USPC .................................................. 514/34, 456
  See application file for complete search history.

(56) References Cited

U.S. PATENT DOCUMENTS

2005/0226943 A1*  10/2005  Yan et al. ...................... 424/725
2010/0151000 A1    6/2010  Thomas et al.

FOREIGN PATENT DOCUMENTS

| KR | 1020090001181 A | 1/2009 |
|---|---|---|
| KR | 1020090010504 A | 1/2009 |
| WO | 2005/095375 A1 | 10/2005 |

OTHER PUBLICATIONS

Boonkaewwan et al. Anti-Inflammatory and Immunomodulatory Activities of Stevioside and Its Metabolite Steviol on THP-I Cells. J Agric Food Chem 54:785-789, 2006.*
Azevedo et al. Cytokine Responses in Gnotobiotic Pigs after Infection with Virulent or Attenuated Human Rotavirus. J Virol 80:372-382, 2006.*
Tsai et al. Effect of Ethanol Extracts of Three Chinese Medicinal Plants With Anti-diarrheal Properties on Ion Transport of the Rat Intestinal Epithelia. I Pharmacol Sci 94:60-66, 2004.*
Starkey et al. Transport of Water and Electrolytes by Rotavirus-Infected Mouse Intestine: A Time Course Study. J Pediat Gastroenterol Nutr 11:254-260, 1990.*
*The Pharmaceutical Society of Japan.* Okayama 2010 Meeting, Mar. 28-30, 2010, Okayama, Japan, 2 pages.
Alcaro et al., "Biocatalysed synthesis of β-*O*-glucosides from 9-fluorenon-2-carbohydroxyesters. Part 3: IFN-inducing and anti-HSV-2 properties," *Bioorganic & Medicinal Chemistry* 13:3371-3378, 2005.
Geiler et al., "N-acetyl-L-cysteine (NAC) inhibits virus replication and expression of pro-inflammatory molecules in A549 cells infected with highly pathogenic H5N1 influenza A virus," *Biochemical Pharmacology* 79:413-420, 2010.
Han et al., "Lavandulyl Flavonoids from *Sophora flavescens* Suppress Lipopolysaccaride-Induced Activation of Nuclear Factor-κB and Mitogen-Activated Protein Kinases in RAW264.7 Cells," *Biol. Pharm. Bull.* 33(6):1019-1023, 2010.
Hwang et al., "BACE1 inhibitory effects of lavandulyl flavanones from *Sophora flavescens*," *Bioorganic & Medicinal Chemistry* 16:6669-6674, 2008.
Takahashi et al., "Analysis of anti-rotavirus activity of extract from *Stevia rebaudiana*," *Antiviral Research* 49:15-24, 2001.

* cited by examiner

*Primary Examiner* — Clinton Brooks
*Assistant Examiner* — Yih-Horng Shiao
(74) *Attorney, Agent, or Firm* — Seed IP Law Group PLLC

(57) ABSTRACT

The present invention relates to a composition for enhancing immunity through inducing the expression of interferon-β comprising a compound represented by Formulas 1 to 8, or *Sophora flavescens* extract comprising the same and fractions thereof as an active ingredient, a feed additive, feed composition, pharmaceutical composition, food composition, and over-the-counter (OTC) drug composition comprising the composition, and a method for enhancing immunity through administrating the composition. A composition for inducing the expression of interferon-β, comprising a compound represented by Formulas 1 to 8 of the present invention, *Sophora flavescens* extract comprising the same, or fractions thereof as active ingredient can prevent, alleviate, or treat the diseases that can be prevented or treated by increasing the expression of interferon.

6 Claims, 14 Drawing Sheets

| Samples | Dose (μM) | Cell viability (%) | CPE reduction assay(%) KJ56-1(Bovine, G8P[7]) |
|---|---|---|---|
| Sophoraflavanone G | 10 | 80.3±0.7 | 64.9±4.8 |
| Kurarinone | 10 | 124.5±1.0 | 22.8±9.3 |
| Isoxanthohumol | 10 | 105.5±7.5 | 3.8±1.7 |
| Leachianone | 10 | 89.8±3.2 | 62.2±6.0 |
| Kushenol A | 10 | 97.5±3.0 | 29.3±12.2 |
| Kushenol T | 10 | 99.6±4.9 | 6.8±1.3 |
| 2'-methoxykurarinone | 10 | 96.5±6.0 | 56.3±6.9 |

Figure 5a

| Piglet No. | time of inocula-tion of virus | dose concentra-tion | severity of diarrhea* | | | | | | | | | |
|---|---|---|---|---|---|---|---|---|---|---|---|---|
| | | | number of days after inoculation | | | | | | | | | |
| | | | 1day | 2day | 3day | 4day | 5day | 6day | 7day | 8day | 9day | 10day |
| 1 | no inoculation | no administration | 0 | 0 | 0 | 0 | 0 | 0 | 0 | 0 | 0 | 0 |
| 2 | no inoculation | no administration | 0 | 0 | 0 | 0 | 0 | 0 | 0 | 0 | 0 | 0 |
| 3 | no inoculation | no administration | 0 | 0 | 0 | 0 | 0 | 0 | 0 | 0 | 0 | 0 |
| 4 | 3days after birth | no administration | 0 | 1 | 2 | 2 | 2 | 2 | 2 | 2 | 2 | 2 |
| 5 | 3days after birth | no administration | 0 | 1 | 2 | 2 | 2 | 2 | 2 | 2 | 2 | 2 |
| 6 | 3days after birth | no administration | 0 | 1 | 2 | 2 | 2 | 2 | 2 | 2 | 2 | 2 |
| 7 | 3days after birth | 100 mg/ml X 4 times administration (1day) | 0 | 1 | 2 | 2 | 2 | 1 | 1 | 1 | 1 | 1 |
| 8 | 3days after birth | 100 mg/ml X 4 times administration (1day) | 0 | 1 | 1 | 1 | 1 | 1 | 1 | 1 | 1 | 1 |
| 9 | 3days after birth | 200 mg/ml X 4 times administration (1day) | 0 | 1 | 1 | 1 | 1 | 1 | 1 | 1 | 1 | 1 |
| 10 | 3days after birth | 200 mg/ml X 4 times administration (1day) | 0 | 1 | 1 | 2 | 2 | 2 | 2 | 1 | 1 | 1 |

*0: normal, 1: paste-like, 2: mucus, 3: liquid-like, 4; high volume of diarrhea, X: death

Figure 5c

| Piglet No. | time of inoculation of virus | dose concentration | severity of lesion[a] | | |
|---|---|---|---|---|---|
| | | | duodenum | duoden-ojejunal | ileum |
| 1 | no inoculation | no administration | 0 | 0 | 0 |
| 2 | no inoculation | no administration | 0 | 0 | 0 |
| 3 | no inoculation | no administration | 0 | 0 | 0 |
| 4 | 3 days after birth | no administration | 4 | 4 | 4 |
| 5 | 3 days after birth | no administration | 4 | 4 | 4 |
| 6 | 3 days after birth | no administration | 4 | 4 | 4 |
| 7 | 3 days after birth | 100 mg/ml x4 times administration | 2.5 | 3 | 3 |
| 8 | 3 days after birth | 100 mg/ml x4 times administration | 2.5 | 3 | 2.5 |
| 9 | 3 days after birth | 200 mg/ml x4 times administration | 2 | 2.3 | 2 |
| 10 | 3 days after birth | 200 mg/ml x4 times administration | 2.2 | 2.5 | 2 |

*Standard for measuring severity is as follows. Ratio of villus and crypt, 0=normal (villus/crypt ≥6:1), 1=light (villus/crypt = 5.0 – 5.9:1), 2=moderate (villus/crypt = 4.0 – 4.9:1), 3=obvious (villus/crypt = 3.0 – 3.9:1), 4=severe (villus/crypt ≤ 3.0:1). Degree of exfoliation of epithelial cells, 0=normal (no exfoliation), 1=light (exfoliation of cuboidal epithelium of upper villus), 2=moderate (exfoliation of epidermal cell of upper villus), 3=obvious (exfoliation of epidermal cell of lowder villus), 4=severe (exfoliation of epidermal cell of crypt)

Figure 6a

| Piglet No. | time of inocula- tion of virus | dose concentra- tion | severity of diarrhea* number of days after inoculation | | | | | | | | | |
|---|---|---|---|---|---|---|---|---|---|---|---|---|
| | | | 1day | 2day | 3day | 4day | 5day | 6day | 7day | 8day | 9day | 10day |
| 1 | no inoc- ulation | no administ- ration | 0 | 0 | 0 | 0 | 0 | 0 | 0 | 0 | 0 | 0 |
| 2 | no inoc- ulation | no administ- ration | 0 | 0 | 0 | 0 | 0 | 0 | 0 | 0 | 0 | 0 |
| 3 | no inoc- ulation | no administ- ration | 0 | 0 | 0 | 0 | 0 | 0 | 0 | 0 | 0 | 0 |
| 4 | 3days after birth | no administ- ration | 0 | 1 | 2 | 2 | 2 | 2 | 2 | 2 | 2 | 2 |
| 5 | 3days after birth | no administ- ration | 0 | 1 | 2 | 2 | 2 | 2 | 2 | 2 | 2 | 2 |
| 6 | 3days after birth | no administ- ration | 0 | 1 | 2 | 2 | 2 | 2 | 2 | 2 | 2 | 2 |
| 7 | 3days after birth | 100 mg/ml Sophora flavescens extract+3g/ml stevioside | 0 | 1 | 2 | 2 | 2 | 1 | 1 | 1 | 1 | 1 |
| 8 | 3days after birth | 100 mg/ml Sophora flavescens extract+3g/ml stevioside | 0 | 1 | 2 | 2 | 2 | 2 | 1 | 1 | 1 | 1 |
| 9 | 3days after birth | 200 mg/ml Sophora flavescens extract+3g/ml stevioside | 0 | 1 | 2 | 2 | 2 | 1 | 1 | 1 | 1 | 1 |
| 10 | 3days after birth | 200 mg/ml Sophora flavescens extract+3g/ml stevioside | 0 | 1 | 1 | 1 | 1 | 1 | 1 | 1 | 0 | 0 |

*0: normal, 1: paste-like, 2: mucus, 3: liquid-like, 4; high volume of diarrhea, X: death

Figure 6c

| Piglet No. | time of inoculation of virus | dose concentration | severity of lesion[a] | | |
|---|---|---|---|---|---|
| | | | duodenum | duoden-ojejunal | ileum |
| 1 | no inoculation | no administration | 0 | 0 | 0 |
| 2 | no inoculation | no administration | 0 | 0 | 0 |
| 3 | no inoculation | no administration | 0 | 0 | 0 |
| 4 | 3 days after birth | no administration | 4 | 4 | 4 |
| 5 | 3 days after birth | no administration | 4 | 4 | 4 |
| 6 | 3 days after birth | no administration | 4 | 4 | 4 |
| 7 | 3 days after birth | 100 mg/ml x4 times administration | 2.75 | 3 | 2.5 |
| 8 | 3 days after birth | 100 mg/ml x4 times administration | 2.3 | 2.5 | 2.5 |
| 9 | 3 days after birth | 200 mg/ml x4 times administration | 2.1 | 2.5 | 2.2 |
| 10 | 3 days after birth | 200 mg/ml x4 times administration | 2.2 | 2.4 | 2.1 |

[a]Histological changes of small intestine are represented by an average of the villus/crypt ratio and degree of exfoliation of epithelial cell. Standard for measuring severity is as follows. Ratio of villus and crypt, 0=normal (villus/crypt ≥6:1), 1=light (villus/crypt = 5.0 – 5.9:1), 2=moderate (villus/crypt = 4.0 – 4.9:1), 3=obvious (villus/crypt = 3.0 – 3.9:1), 4=severe (villus/crypt ≤ 3.0:1). Degree of exfoliation of epithelial cells, 0=normal (no exfoliation), 1=light (exfoliation of cuboidal epithelium of upper villus), 2=moderate (exfoliation of epidermal cell of upper villus), 3=obvious (exfoliation of epidermal cell of lowder villus), 4=severe (exfoliation of epidermal cell of crypt)

COMPOSITION FOR ENHANCING IMMUNITY CONTAINING COMPOUNDS REPRESENTED BY CHEMICAL FORMULAS 1-8 OR SOPHORA FLAVESCENS EXTRACT AS ACTIVE INGREDIENT

TECHNICAL FIELD

The present invention relates to a composition for enhancing immunity through inducing the expression of interferon-β comprising a compound represented by Formulas 1 to 8, or *Sophora flavescens* extract comprising the same and fractions thereof as an active ingredient, a feed additive, feed composition, pharmaceutical composition, food composition, and over-the-counter (OTC) drug composition comprising the composition, and a method for enhancing immunity through administrating the composition.

BACKGROUND ART

Interferon was first found in cytokines which are produced in the virus-infected cells and is known as the cytokine with the most remarkable antiviral activity.

Although interferon was first found as a compound with inhibitory effect against influenza virus or other viruses while being produced from the influenza virus-infected chick embryonic cells, there have been many attempts to use interferon for treating other types of diseases after its discovery. As a result, it has been found that interferon can be used for the treatment of various viral diseases, chronic hepatitis B and C, hematologic malignancy, and multiple sclerosis. The effects and stability of interferon were confirmed especially in the patients with Immunocompetence. In addition, it was recently found that interferon has inhibitory effect against HIV infection. Therefore, increasing the expression of interferon can enhance the immunity.

In general, virus can infect various hosts including humans, animals, plants, and microorganisms (Patton J T, Caister Academic Press, 2008). Among those virus, rotavirus which is a type of dsRNA virus belongs to Reoviridae family and it is one of the main causes of severe diarrhea worldwide in young animals (including cow, pig, dog, and goat) and infants. In addition to severe diarrhea, rotavirus may also cause encephalitis, otitis media, necrotizing colitis, hepatapostema, and intussusception (Ester, M. K. Fields Virology, 2001, 1747-1785). In order to treat the rotavirus-associated diseases, methods for direct targeting of virus have been developed such as reducing the absorption of virus to epithelial cells, reducing the invasion of cell by virus, inhibiting transcription and replication of viral genes and protein synthesis, and inhibiting virus release from cell. Until now, numerous vaccines targeting rotavirus have been developed. Also, animal-human recombinant virus vaccine is prepared and manufactured for human treatment by recombining rotavirus from human and animal. The representative animal-human recombinant virus vaccine is a vaccine prepared by inserting the gene encoding for human rotavirus serotype VP4 into a cow rotavirus WC3 as a template, and the vaccine from RotaTeq—Merck was approved by FDA in 2006 and has been sold. However the recombinant virus vaccine may cause side effects such as intrussusception, and thus it involves a huge disadvantage in that it cannot be used for preventing other rotavirus serotypes. To overcome the disadvantage of vaccine, there have been studies on natural products that can suppress rotavirus. As an example, Takahashi et al. have reported that hot water extracts of *Stevia* have anti-rotavirus effects (Takahashi, K et al., Antiviral Res. 2001, 49, 15-24). However, when the natural products or vaccines are used for direct targeting of virus, this may cause virus to acquire resistance to antiviral agents and also other mutations at a high frequency. Therefore, in order to resolve this problem, a lot of studies have focused on developing a method for accompanying the suppression of the excessive inflammatory response of host which is induced by infection, rather than killing the virus itself, so that a severe inflammatory disease by viral infection can be prevented (Geller J. et al, Biochemical Pharmacology, 2010, 413-420).

For a number of years, the genetic engineering or bioengineering approaches have been used to produce a large scale of interferons for developing an antiviral agent and immune enhancing agent. Recently, there have been many studies on investigating the natural products or synthetic chemicals to identify the compound that can induce an interferon activity. However, the compound that shows a high inductive effect of interferon in humans has not been identified yet (Alcaro S et al., Bioorg Med Chem. 2005, 13(10), 3371-3378). Although 3M Pharmaceuticals has developed a strong interferon inducer called Imiquimod(1), there have been multiple side effects identified from its clinical tests, stopping the inducer from being commercialized.

DISCLOSURE

Technical Problem

The present invention relates to a composition for enhancing immunity through inducing the expression of interferon-β comprising a compound represented by Formulas 1 to 8, or *Sophora flavescens* extract comprising the same and fractions thereof as an active ingredient, a feed additive, feed composition, pharmaceutical composition, food composition, and over-the-counter (OTC) drug composition comprising the composition, and a method for enhancing immunity through administrating the composition.

The present inventors have found that *Sophora flavescens* extract, fractions thereof, or the flavanone-type compounds derived therefrom enhance the expression of interferon-β when administered at a concentration not inducing cytotoxicity, which in turn inhibits the proliferation of rotavirus, suggesting that they can be used as a composition for enhancing immunity, thereby completing the present invention.

Technical Solution

An object of the present invention is to provide a composition for enhancing immunity through induction of the expression of interferon-β, comprising any one of the compounds represented by Formulas 1 to 8 or a pharmaceutically acceptable salt thereof as an active ingredient.

Another object of the present invention is to provide a composition for enhancing immunity through induction of the expression of interferon-β, comprising any one of the compounds of claim 1, and *Sophora flavescens* extract or fractions thereof as an active ingredient.

Another object of the present invention is to provide a feed additive, feed composition, pharmaceutical composition, over-the-counter (OTC) drug composition, and food composition comprising the composition of the present invention.

Yet another object of the present invention is to provide a feed additive, feed composition, OTC drug composition, food composition, and pharmaceutical composition comprising the composition of the present invention for the prevention or alleviation of more than one of the diseases selected from the group consisting of infectious diseases including rotavirus, porcine reproductive and respiratory syndrome virus, Coxsackievirus, Colorado tick fever virus, reovirus, human immunodeficiency virus, and hepatitis B and C; inflammation including atopic dermatitis, psoriasis, Anaphylaxis and dermatitis, and IgE-mediated(type) hyperergia; Ocular disease including diabetic retinopathy, retinitis, maculopathy, uveitis, and conjunctivitis; angiosis including stroke, vessel disease, myocardial infarction, unstable angina, angiitis, vascular sclerosis, angiostenosis, Wegener's granulomatosis, Churg-Strauss angiitis, Henoch-Schonlein purpura, Kawasaki disease, and giant cell arteritis; and ankylosing spondylitis, osteoporosis, allergy, diabete mellitus, diabetic nephropathy, acute childhood diabetes, Addison's disease, Goodpasture's sydrome, IgA nephropathy, Bright's disease, nephritis, sjogren's syndrome, auto-immune pancreatitis, periodontal disease, chronic obstructive pulmonary disease, acute leukemia-mediated pulmonary damage, asthma, graft versus host disease, chronic pelvic inflammatory disease, endometritis, rhinitis, metastasis, transplant rejection, stroke, encephalitis, meningitis, AIDS-dementia, fibrosis, adhesion formation, chronic hepatitis, osteosarcoma, basal cell carcinoma, cervix dysplasia, neuroglioma, acute myelogenous leukemia, multiple myeloma, Hodgkin's disease, breast cancer, melanoma, papilloma virus, viral hepatitis, herpes genitalis, herpes zoster, vesicular keratitis, herpes simplex, viral encephalitis, giant cell pneumonia, viral coryza, Chronic hepatitis C, Alzheimer's disease, Creutzfeld-Jakob disease, Gerstmann-Straussler-Scheinker Disease, severe acute respiratory syndrome, stroke, temporary ischaemic attacks and chronic prostatitis.

Another object of the present invention is to provide a method for enhancing immunity of the immunodepressed subject, comprising the step of administrating the composition to the immunodepressed subject.

Yet another object of the present invention is to provide a method for treating rotavirus-mediated diseases, comprising the step of administrating the composition to the rotavirus-infected subject.

Advantageous Effects

A composition for enhancing immunity through induction of the expression of interferon-β, comprising a flavanone-type compound of the present invention, *Sophora flavescens* extract comprising the same, or fractions thereof as an active ingredient can be used in a form of feed additive, feed composition, food composition, OTC drug composition, and pharmaceutical composition and it can prevent, alleviate, or treat the diseases that can be prevented or treated by increasing the expression of interferon.

DESCRIPTION OF DRAWINGS

FIG. 5a shows the evaluation of the effects of *S. flavescens* extract on alleviation of the symptoms of rotavirus-induced porcine diarrhea.

FIG. 5C shows the measurement of histological changes in digestive organs as represented by an average of the ratio of villus and crypt and degree of exfoliation of epithelial cells, demonstrating the therapeutic effects of *S. flavescens* extract on the lesion of digestive organ which is caused by rotavirus infection.

FIG. 6a shows the analysis of the effect of co-administration of *S. flavescens* extract and stevioside on alleviation of the symptoms of rotavirus-induced porcine diarrhea.

FIG. 6c shows the measurement of histological changes in small intestine as represented by an average of the ratio of villus and crypt and degree of exfoliation of epithelial cells, demonstrating the therapeutic effects of *S. flavescens* extract and stevioside on the lesion development in digestive organ which is caused by rotavirus infection.

BEST MODE

Figure 1A:
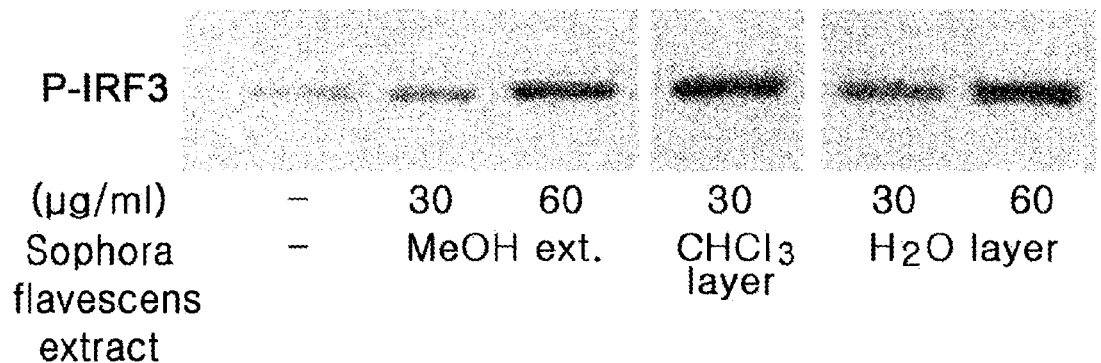
FIG. 1a shows the inductive effect of *S. flavescens* extract and fractions thereof on the phosphorylation of IRF3 in THP-1 cell.

As one aspect to achieve the above objects, the present invention provides a composition for enhancing immunity through induction of the expression of interferon-β, comprising any one of the compounds represented by Formulas 1 to 8 or a pharmaceutically acceptable salt thereof as an active ingredient.

As another aspect, the present invention provides a composition for enhancing immunity through induction of the expression of interferon-β, comprising any one of the compounds represented by Formulas 1 to 8, and *Sophora flavescens* extract or fractions thereof as an active ingredient.

As used herein, 'the compounds represented by Formulas 1 to 8' can be prepared by those skilled in the art according to the conventional method in the art. For instance, the compounds represented by Formulas 1 to 8 can be separated and purified from the plants that are known to comprise the same in the art by using a polar or non-polar solvent, or such compounds may be commercially available. All of the compounds represented by Formulas 1 to 8 are flavanone-type compound, and preferably they can be extracted from *Sophora flavescens*.

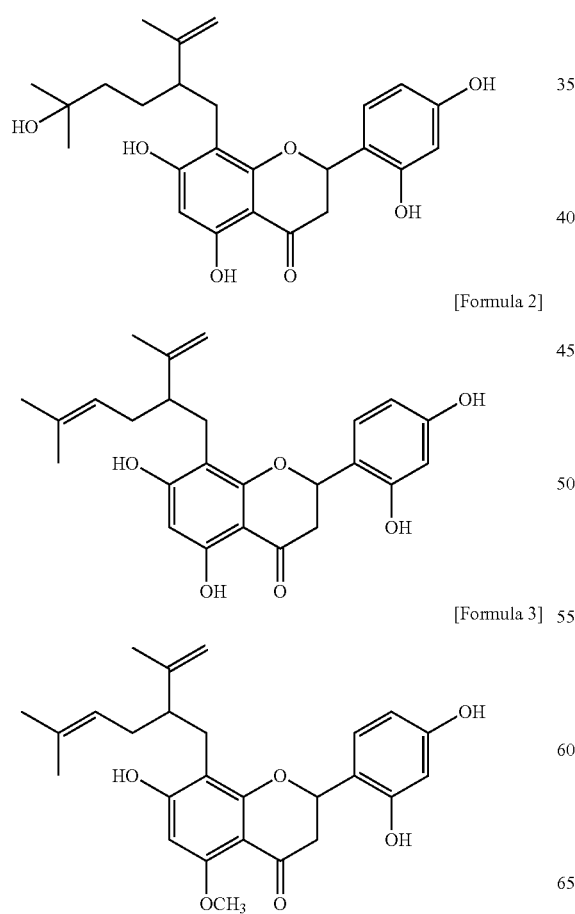

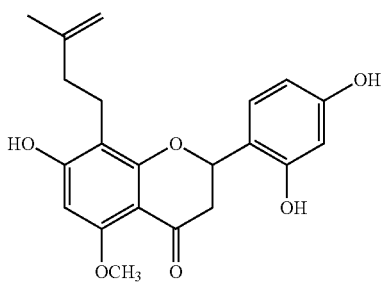

[Formula 4]

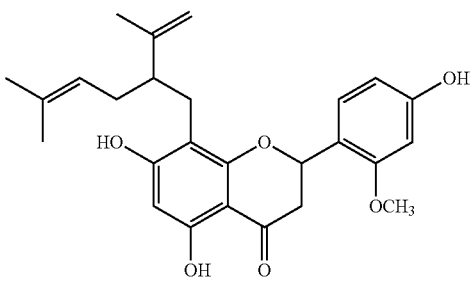

[Formula 5]

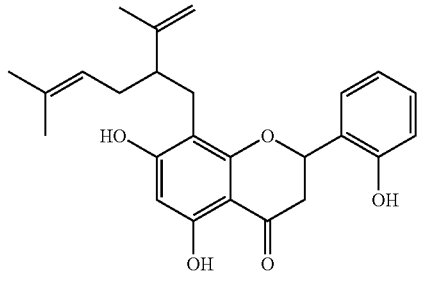

[Formula 6]

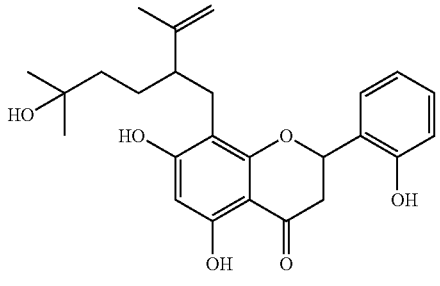

[Formula 7]

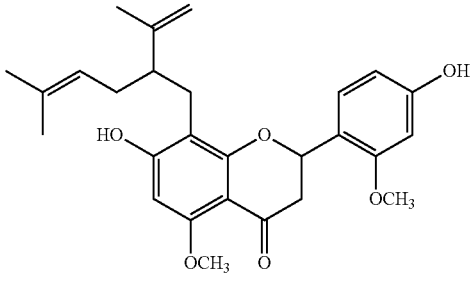

[Formula 8]

As used herein, "pharmaceutically acceptable salt" refers to all salts of the compounds of the present invention (e.g., those obtained by reacting with acid or base) that are physiologically acceptable to animal recipients (e.g., mammals). The salts of the compounds of the present invention can be derived from organic or inorganic acids, and organic or inorganic bases. Examples of the acids include hydrochloric acid, bromic acid, surfuric acid, nitric acid, perchloric acid, fumaric acid, malic acid, phosphoric acid, glycolic acid, latic acid, salicyl acid, succinic acid, toluene-p-surfuric acid, tartaric acid, acetic acid, citric acid, methanesulfonic acid, ethanesulfonic acid, formic acid, benzoic acid, malonic acid, sulfonic acid, naphthalene-2-sulfonic acid, and benzyl sulfonic acid, but are not limited thereto. Also, while pharmaceutically unacceptable by itself, other acids such as oxalic acid can be used for production of useful salts, as an intermediate for preparation of the compound of the present invention and pharmaceutically acceptable addition salts thereof. Example of base includes alkali metal (e.g., sodium) hydroxide, alkali earth metal (e.g., Magnesium) hydroxide, and ammonia, but is not limited thereto. Example of salt includes acetate, adipate, alginate, aspartate, benzoate, benzyl sulfonate, bisulfate, butylate, citrate, camphorate, camphosulfonate, cyclopentanepropionate, digluconate, dodecyl sulfate, ethane sulfonate, fumarate, glucoheptonate, glycerophosphate, hemisulfate, heptanoate, hexanoate, chloride, bromide, iodide, 2-hydroxyethanesulfonate, lactate, malate, methanesulfonate, 2-naphthalene sulfonate, nicotinate, oxalate, pamoate, pectinate, persulfate, phenyl propionate, picrate, pivalate, propionate, succinate, tartrate, thiocyanate, tosylate, undecanoate, and analogs thereof, but is not limited thereto. Examples of other types of salts include anions of the present compounds that combine with appropriate amount of Na+, $NH_4+$, NW$_4$+ (here, W indicates an alkyl group of C1 to C4), and other similar cations. In order to be used as pharmaceutical agent, the salts of the compounds of the present invention refer to pharmaceutically acceptable salts. However, the salts of pharmaceutically unacceptable acids and bases can also be used for preparation or purification of pharmaceutically acceptable compounds.

As used herein, the *Sophora flavescens* extract refers to the extract obtained by using a solvent selected from the group consisting of water, a $C_1$-$C_4$ lower alcohol, and a mixed solvent thereof, preferably methanol, ethanol, or butanol. Also, as used herein, the extract includes any one of the following: an extract obtained by extraction process, a dilution or concentrate of the extract, a dried extract obtained by drying the extract, or a crude extract or purified extract.

A method for preparing *Sophora flavescens* extract in the present invention is as follows. A polar solvent like $C_1$ to $C_4$ lower alcohol such as water, methanol, ethanol, and butanol or a mixture solvent mixed in a ratio of 1:0.1 to 1:10 is used as an extraction solvent, and the extraction solvent is used in a volume of 2 to 20 times, preferably 3 to 5 times, of the dry weight of *sophora* root. The extraction is performed at the temperate of 20 to 100° C., preferably at a room temperature. The extraction duration is for about 12 hours to 4 days, preferably for 3 days. The method for extraction can be hot water extraction, cold water extraction, reflux cooling extraction, or ultrasound extraction. Preferably the *sophora* root is extracted with cold water for 1 time to 5 consecutive times and vacuum filtered, and then the filtered extract is concentrated down through vacuum evaporation by using a rotary vacuum evaporator at 20 to 100° C., preferably at a room temperature. Through this method, *sophora* crude extract that is soluble in water, lower alcohol, or a mixture solvent thereof can be obtained.

In the present invention, solvent fractions of *S. flavescens* extract can be obtained as a polar fraction and non-polar fraction by suspending the *S. flavescens* extract in water and then fractionating the suspended extract with non-polar solvent such as n-hexane or chloroform. In one of the Examples of the present invention, water fraction and chloroform fraction were prepared as solvent fraction.

Methods for collecting the fractions of *S. flavescens* extract in the present invention are as follows. The crude extract of *S. flavescens* obtained by the above-described method is suspended in distilled water, and mixed with non-polar solvents such as hexane, ethyl acetate, or chloroform in the amount of 1 to 100 times, preferably 1 to 5 times, of the volume of the suspension. Then the soluble layer in non-polar solvent can be collected by extracting and separating the soluble layer for 1 to 10 times, preferably 2 to 5 times. Furthermore, other common fractionation can be performed additionally (Harborne J. B. Phytochemical methods: *A guide to modern techniques of plant analysis*, 3rd Ed. p6-7, 1998). To be specific, after suspending the crude extract of *S. flavescens* in water, soluble extract of *S. flavescens* in each solvent can be collected by continuous extraction using equivalent amount of n-hexane and chloroform as solvent. To be more specific, after suspending the crude extract of *S. flavescens* in water, the suspension is mixed with equivalent amount of n-hexane and then fractionated to collect n-hexane soluble fraction and water soluble fraction. The water soluble fraction can be further fractionated with chloroform and separated into chloroform soluble fraction and water soluble fraction.

These *S. flavescens* extract or fractions thereof can comprise any one of the compounds represented by Formulas 1 to 8.

Also, a composition for enhancing immunity through induction of the expression of interferon-β in the present invention may comprise any one of the compounds represented by Formulas 1 to 8, a pharmaceutically acceptable salt thereof, or *S. flavescens* extract comprising any one of the compounds or fractions thereof, and additionally more than one substances that are known to induce interferon-β expression in the art. For example, the composition of the present invention may further comprise *Stevia rebaudiana* extract or stevioside.

As used herein, "*Stevia rebaudiana*" is a dicotyledon and perennial plant in the family Compositae and order Campanulales. It grows near river or wetland. In terms of root development, it has a lot of lateral roots and adventive-roots and the development of main root is not clear. During the rest period of plant growth, a thick root is formed developing a storing function. A new branch grows out from a latent bud near roots forming a new stem every year. A stem grows straight up and loses its function during winter. Stem nodes hold leaves and branches grow in leaf axils. Leaves grow facing each other and have a form of lancet, a length of 4 to 10 cm, and a width of about 2.5 cm. Also, leaves are thin saw-like and have curves. There are three veins and no petiole, and there are fluffs on entire leaves. Five to six tubular flowers bloom together per each flower, and *S. rebaudiana* are self-incompatible. As *S. rebaudiana* is a short-day plant, the flowers bloom faster under short-day conditions. The seed of *S. rebaudiana* has very low rate of sprouting and the front tip of seed has a pappus having a shape of the ribs of a fan. Its place of origin is border mountain area such as Paraguay, the Argentine Republic, and Brazil of South America. *Stevia* leaves have been used as a sweetener in Paraguay from long ago, and as the harmful effects of a synthetic sweetener saccharin became an issue recently, *Stevia* leaves attracts the attention again. It is known that *Stevia* leaves contain stevioside which is a sweetening substance by 6 to 7% of total weight, but the percentage of stevioside varies a lot depending on the subjects. Sweetness of stevioside is 300 times greater than sugar, and it can be prepared as a tea, used as a gum and a sweetener for soft drinks. *S. rebaudiana* was first introduced in Korea in 1973, and a cultivation test was performed to develop an alternative of sugar in National Crop Experiment Station and *S. rebaudiana* was also grown in farms. Species nurtured in Korea are Suwon No. 2 (sweetening substance 12.2%) and Suwon No. 11 (23%). Breeding of *S. rebaudiana* is done by spreading seeds and planting a cutting. Harvesting can be done once or twice per year, and early or middle September is a right time for harvesting.

Figure 6B:
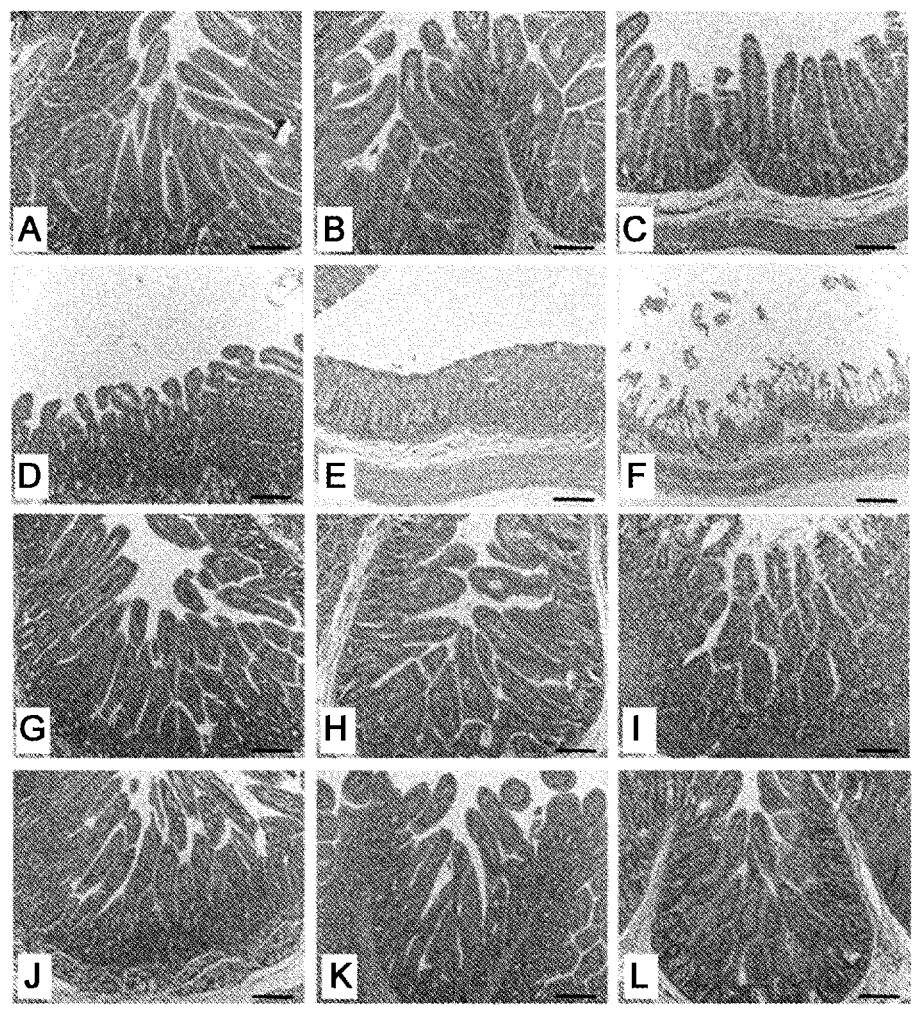
FIG. 6b shows the comparison of the histological changes in digestive organs, demonstrating the therapeutic effects of co-administration of *S. flavescens* extract and stevioside on lesion development in digestive organ which is caused by rotavirus infection.

As used herein, "stevioside" is a glycoside contained in *stevia* leaves and is a natural sweetener giving 300 times sweeter flavor than sugar. In many countries such as Paraguay, Brazil, and Japan, stevioside is used as a low-calorie sweetener. Normally stevioside has been used in beverage, soy sauce, alcoholic beverages, and snacks, but it has been reported that when it reacts with alcohol, it gets transformed into a toxic substance steviol, and thus in a developed country, adding stevioside to alcohol beverages is prohibited. On the other hand, stevioside is used as a sweetener for an alcoholic beverage such as Soju in Korea. In one Example of the present invention, it was observed that when stevioside was co-administered with the medicine, the symptom of porcine diarrhea by rotavirus infection could be alleviated (FIG. 6a), and the lesion in digestive organ induced by rotavirus infection could be treated by greater extent (FIGS. 6b and 6c).

Figure 1B:
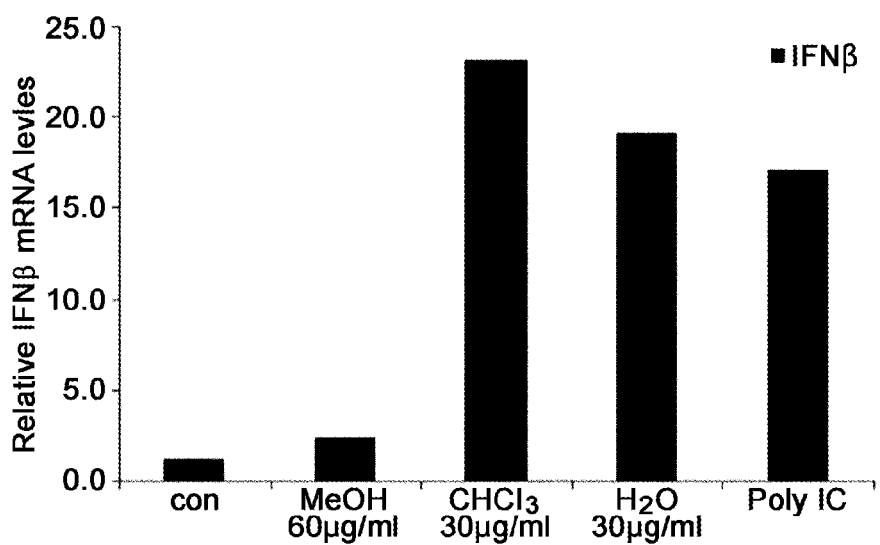
FIG. 1b shows the inductive effect of *S. flavescens* extract and fractions thereof on the expression of interferon-β (IFN-β) mRNA in THP-1 cells.
Figure 2A:
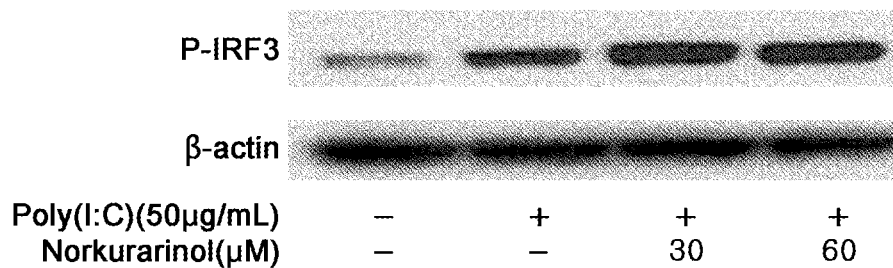
FIG. 2a shows the inductive effect of the compound of Formula on the expression of IRF3 which is activated and phosphorylated by poly(I:C) treatment in THP-1 cells.
Figure 2B:
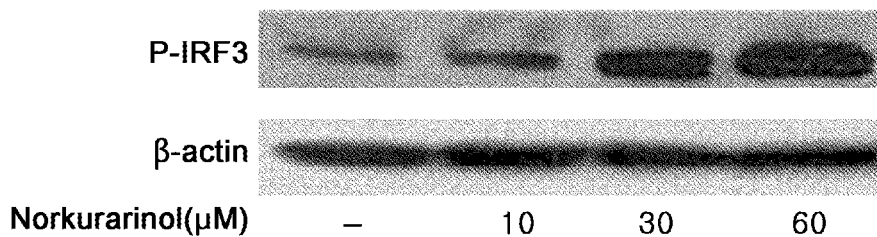
FIG. 2b shows the inductive effect of the compound of Formula 1 on the phosphorylation of IRF3 in THP-1 cells.
Figure 2C:
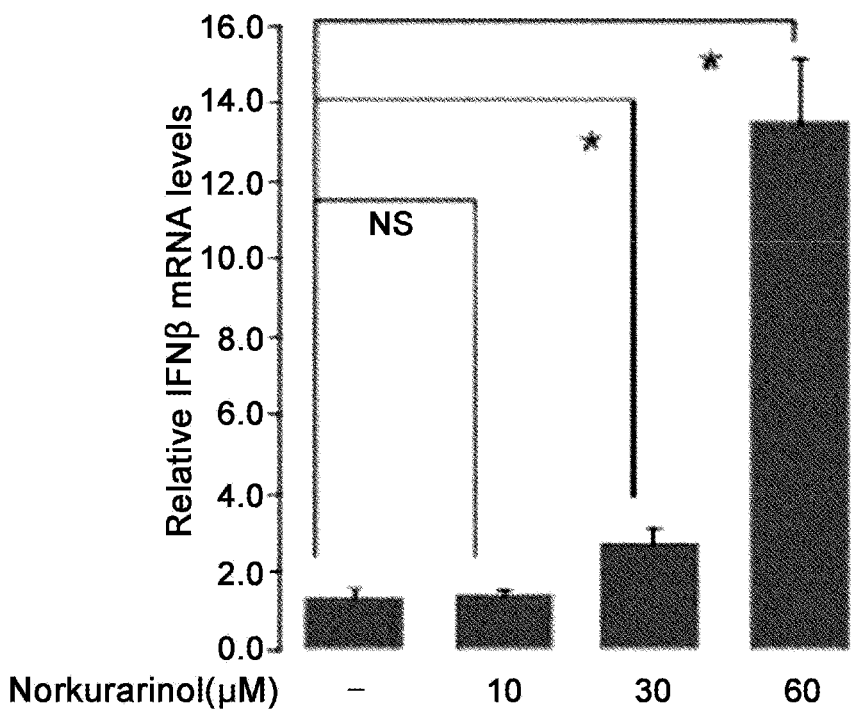
FIG. 2c shows the inductive effect of the compound of Formula 1 on the expression of IFN-β mRNA in THP-1 cells.
Figure 4B:
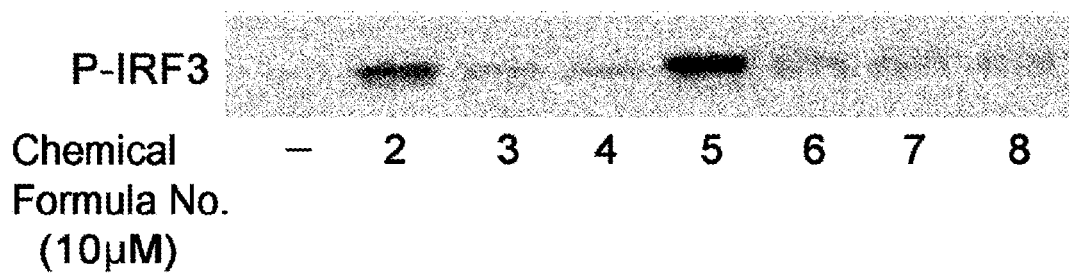
FIG. 4b shows the inductive effect of the compounds represented by Formulas 2 to 8 on phosphorylation of IRF3 in THP-1 cells.
Figure 4C:
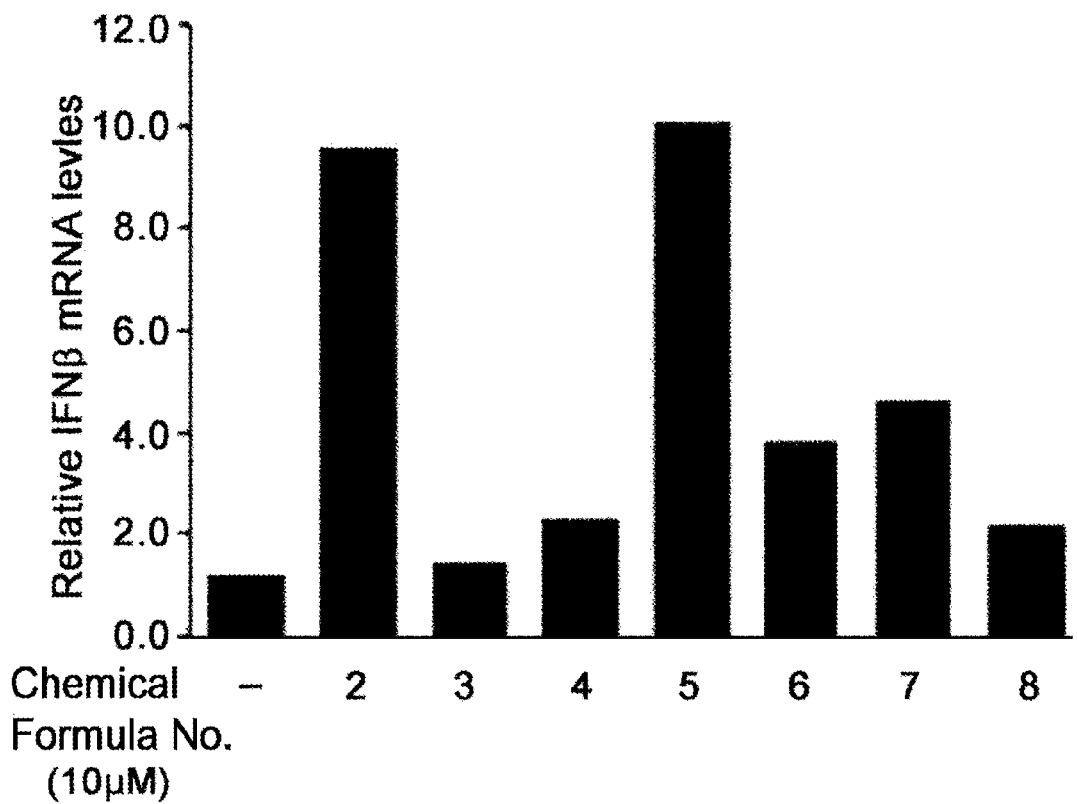
FIG. 4c shows the inductive effect of the compound represented by Formulas 2 to 8 on the expression of IFN-β mRNA in THP-1 cells.

A composition for enhancing immunity through induction of the expression of interferon-β in the present invention may comprise any one of the compounds represented by Formulas 1 to 8, a pharmaceutically acceptable salt thereof, or *S. flavescens* extract comprising any one of the compounds or fractions thereof, wherein these compounds show an antiviral actions by having immune-enhancing activity that activates IRF-3 and induces interferon expression. In this regard, the present inventors have confirmed that a methanol extract, chloroform fraction, and water fraction of *S. flavescens* induce phosphorylation of IRF-3 (FIG. 1a) and increase the expression level of interferon (FIG. 1b). Furthermore, the present inventors have found that the compounds represented by Formulas 1 to 8 of the present invention induce phosphorylation of IRF-3 (FIGS. 2a and 4b) and increase the expression level of interferon (FIGS. 2c and 4c).

As used herein, "interferon-β (INF-β)" refers to a protein that is excreted by the cell of animal body in a response to the invasion of pathogen such as virus or foreign substance such as tumor cells. Interferon-β is a type of cytokine that suppresses the proliferation of virus or cells and regulates the immune system and inflammation. It is known that the activation of Interferon-β is directly induced by viral infection and dsRNA. Interferon-α and -β are produced in various types of cells such as lymphocyte including T cells and B cells, macrophage, fibroblast, vascular endothelial cell, and osteoblast, and is an important factor for inducing an antiviral reaction. Interferon-α and -β stimulate both macrophage and natural killer (NK) cells, and directly suppress the proliferation of tumor cells. Furthermore, interferon-β is used for suppression and inhibition of relapse of hepatitis C, cirrhosis and multiple sclerosis.

Any one of the compounds represented by Formulas 1 to 8, a pharmaceutically acceptable salt thereof, or *Sophora flavescens* extract comprising any one of the compounds or fractions thereof can induce the expression of interferon-β, therefore they can be used for treating the diseases that can be prevented or treated by an increase in interferon-β expression.

Examples of the "disease that can be prevented or treated by an increase in interferon-β expression" include infectious diseases including rotavirus, porcine reproductive and respiratory syndrome virus, Coxsackievirus, Colorado tick fever virus, reovirus, human immunodeficiency virus, and hepatitis B and C; inflammation including atopic dermatitis, psoriasis, Anaphylaxis and dermatitis, and IgE-mediated(type) hyperergia; Ocular disease including diabetic retinopathy, retinitis, maculopathy, uveitis, and conjunctivitis; angiosis including stroke, vessel disease, myocardial infarction, unstable angina, angiitis, vascular sclerosis, angiostenosis, Wegener's granulomatosis, Churg-Strauss angiitis, Henoch-Schonlein purpura, Kawasaki disease, and giant cell arteritis; and ankylosing spondylitis, osteoporosis, allergy, diabete mellitus, diabetic nephropathy, acute childhood diabetes, Addison's disease, Goodpasture's sydrome, IgA nephropathy, Bright's disease, nephritis, sjogren's syndrome, auto-immune pancreatitis, periodontal disease, chronic obstructive pulmonary disease, acute leukemia-mediated pulmonary damage, asthma, graft versus host disease, chronic pelvic inflammatory disease, endometritis, rhinitis, metastasis, transplant rejection, stroke, encephalitis, meningitis, AIDS-dementia, fibrosis, adhesion formation, chronic hepatitis, osteosarcoma, basal cell carcinoma, cervix dysplasia, neuroglioma, acute myelogenous leukemia, multiple myeloma, Hodgkin's disease, breast cancer, melanoma, papilloma virus, viral hepatitis, herpes genitalis, herpes zoster, vesicular keratitis, herpes simplex, viral encephalitis, giant cell pneumonia, viral coryza, Chronic hepatitis Alzheimer's disease, Creutzfeld-Jakob disease, Gerstmann-Straussler-Scheinker Disease, severe acute respiratory syndrome, stroke, temporary ischaemic attacks and chronic prostatitis, but are not limited thereto.

The multiple sclerosis refers to chronic neuroimmunologic disorder that occurs in central nervous system including brain, spinal cord, and optic nerve. The mechanism in pathogenesis of multiple sclerosis is not fully understood yet, but according to many studies, this disease is mainly caused by abnormal immune response which damages myelin sheaths around the axons.

Currently, there is no medicine for complete treatment of multiple sclerosis. However, there are several medicines developed for alleviating the onset or development of the disease and interferon-β is one of the representative medicines. In 1993, interferon β-1b was first approved by FDA as a medicine for treating multiple sclerosis, and then two other types of interferon beta-1a were developed consecutively and have been used in treatment of disease. The interferon-β medicine has the above-described therapeutic effects along with an excellent tolerability and long-term stability, and thus it has been used the most for the treatment of multiple sclerosis. Recently, the importance of an early diagnosis and early treatment has been emphasized for the best possible therapeutic results. Likewise, an early interferon-β treatment of the patients who are diagnosed with a clinically isolated syndrome, which can develop into multiple sclerosis at high chance, has been supported by national healthcare insurance program in Korea since 2013.

About 5% of the world population and about 8 to 12% of the population in Korea are infected with hepatitis B. Through continuous proliferation of virus, Hepatitis B can lead to cirrhosis and primary liver cancer, becoming the $9^{th}$ leading cause of death worldwide. In order to treat chronic viral hepatitis, either or both of antiviral medicine such as Adenine arabinoside and Acyclovir and immunosuppressant such as Azathioprine and adrenal cortex hormone have been used, however the antiviral activity of these medicines is weak, and when administered for a long period of time, they may cause side effects and thus there are still many limitations for clinical application of them. In contrast, interferon was first used in 1975 for the treatment of hepatitis B, and since then it has shown an excellent antiviral effect, antiproliferative effect, and immune-regulatory effect. Furthermore, in 1992 interferon-$a_{2b}$ was approved by FDA and since then, interferon has been widely used for treatment of chronic viral hepatitis.

As another aspect, the composition for enhancing immunity of the present invention can be used as a feed additive, and thus the present invention provides a feed additive comprising the composition for enhancing immunity or a feed composition comprising the feed additive.

As used herein, "feed additive" refers to a substance that is added to animal feed for various purposes such as supplementing nutrition and preventing weight loss, enhancing digestion of fibers within the feed, improving milk quality, preventing reproductive disorders and improving pregnancy rate, and preventing a high-temperature stress during summer season. The feed additive of the present invention refers to feed supplements approved by Control of Livestock and Fish Feed Act, and examples of such feed additive include mineral formulation including sodium hydrogen carbonate (sodium bicarbonate), bentonite, magnesium oxide, mineral drugs such as complex minerals, and trace minerals such as zinc, copper, cobalt, and selenium; vitamins including carotene, vitamin E, vitamins A, D, E, nicotinic acid, vitamin B complex; amino acid protective agents including methionine and lysine; fatty acid protective agents such as fatty acid calcium; live bacterial cell and yeast including probiotic (lactic acid bacteria), yeast culture, and fungus culture.

The feed composition comprising the composition for enhancing immunity in the present invention can be prepared according to various known methods for preparing feed in the art by adding any of the compounds represented by Chemical Formulas 1 to 8 or pharmaceutically acceptable salts thereof, or *Sophora flavescens* extract comprising any of the compounds or fractions thereof with an appropriate and effective concentration range.

As used herein, "feed" refers to any natural or artificial diet, meal or substance of the meal for animals to eat, intake, and digest or suitable for this purpose.

To be specific, the feed of the present invention comprising the composition for enhancing immunity as an active ingredient can be prepared in various forms known in the art, and preferably a concentrated feed, bulky feed and/or specialty feed may be used. Types of concentrated feed are seed-bearing plants including grains such as wheat, oat, and corn; bran including rice bran, wheat bran, and barley bran which is by-product from refining grains; dregs collected after extracting oil from bean, fluid, sesame, linseed, coconut palm; residues such as leftovers after extracting starch from sweet potato or potato; fish soluble which is a concentrate of fresh liquid obtained from fish meals, fish residues, and fishes; animal feeds such as dried whey obtained by drying the remaining liquid or whey after preparing cheese from meat scrap, blood powder, feather meal, skimmed milk powder, and milk and preparing casein from skim milk; yeast; chlorella; seaweed.

Types of bulky feed include green forage feed such as wild grass, grass, soiling crop; root vegetables such as feed turnip, feed beet, rutabaga which is a type of turnip; silage prepared by lactic-acid-fermentation of green forage, soiling crop, and grain filled in silo; hay prepared by drying wild grass and grass; straw of crops for breeding stock; and leaves of beans and plants.

Types of specialty feed include mineral feed such as oyster shell and rock salt; urea feed including urea or derivative thereof such as isobutane diureide; and a feed additive or dietary supplement which is added in a trace amount as a supplement for a lacking substance in assorted feed made of natural ingredients or to improve the storage duration of feed.

A "dietary supplement" is a composition contained in a medicine provided to animals, for example a medication or digestant. It is not a usual source of calorie intake for body, i.e. source of energy, but rather it refers to a composition added to a common animal feed and taken together.

Also, the "food additive" refers to a substance added to food in a small amount for the purpose of improving appearance, flavor, constitution or storability. Furthermore, it refers to a substance used for improving the quality of food, thereby improving preservability or palatability and also the nutritional value and substantial value of foods. In other words, as defined in Article 2(2) of Food Sanitation Act, a food additive is a substance added, mixed, or infiltrated into food for production or preservation of food product.

The type of subject for the feed composition of the present invention is not typically limited and thus as long as the subject is supplied with the feed composition for the purpose of improving its immunity through inducing interferon-β expression, the feed composition can be applied to any type of subjects. For example, the feed composition can be applied to the subjects including non-human animals such as a monkey, dog, cat, rabbit, guinea pig, rat, mouse, cow, sheep, pig, and goat; birds; and fish.

The present inventors have confirmed that *S. flavescens* extract of the present invention has therapeutic effects in diarrhea and lesion in digestive organ which are caused by rotavirus infection in pigs (FIGS. 5 to 6), thereby demonstrating that the compound, or *S. flavescens* extract or fractions thereof of the present invention can enhance immunity through inducing interferon-β expression.

As another aspect, the present invention provides a pharmaceutical composition comprising the composition for enhancing immunity.

The pharmaceutical composition of the present invention may be formulated in any one of the forms selected from the group consisting of tablets, pills, powders, granules, capsules, suspension, solutions, emulsions, syrups, sterilized aqueous solution, non-aqueous solution, lyophilized formulation and suppository.

The pharmaceutical composition of the present invention may comprise pharmaceutically acceptable carriers. The composition comprising pharmaceutically acceptable carriers may be in a form of various oral or parenteral formulations. The composition is formulated with conventional diluents or excipients, including fillers, extenders, binders, wetting agents, disintegrants, and surfactants.

Solid formulations for oral administration include tablets, pills, powders, granules, and capsules. These solid formulations are prepared by mixing one or more compounds with at least one of excipients, for example, starch, calcium carbonate, sucrose, lactose, and gelatin. Also, other than the simple excipients, lubricants such as magnesium stearate and talc are used as well. In addition, types of liquid formulation for oral administration include a suspension, solution, emulsion and syrup. To this liquid formulation, not only a commonly used diluent such as water and liquid paraffin may be added, but also various types of excipients such as wetting agents, sweetening agents, flavors, and preservatives can be included. Types of formulations for parenteral administration include sterilized aqueous solutions, non-aqueous solutions, suspensions, emulsions, lyophilized formulation, and suppositories. As non-aqueous solvent and suspending agent, propylene glycol, polyethylene glycol, vegetable oils such as olive oil, and injectable esters such as ethyl oleate may be used. The base composition for suppository may include witepsol, macrogol, tween 61, cacao butter, laurin butter, and glycerinated gelatin.

As described above, the pharmaceutical composition of the present invention may comprise a pharmaceutically acceptable salt. Meanwhile, a dose of composition to be administrated in a subject, an effective dose concentration, and a method for administration can be easily determined by those skilled in the art through using the well-known skills in the art as described above. The composition of the present invention is administered in a pharmaceutically effective amount. As used herein, the term "pharmaceutically effective amount" refers to an amount sufficient to suppress or relieve pruritus, at a reasonable benefit/risk ratio applicable to any medical treatment. The effective dosage level of the composition may be determined by the factors including a type of subject, severity of condition, an age and sex of subject, an activity of drug, a sensitivity towards drug, duration and route of administration, excretion rate, duration of treatment, a type of drugs used in combination with the composition, and other factors well-known in the medical field. The pharmaceutical composition of the present invention may be administered alone or in combination with other medicines. Likewise, the present composition may be administered sequentially or simultaneously with conventional medicines. Also, the present composition may be administered in single or multiple doses. In view of all of these factors, it is important to administer the composition in a minimum amount yielding the maximum possible effect without causing side effects and this pharmaceutically effective amount can be easily determined by those skilled in the art.

The type of subjects for the feed composition of the present invention not typically limited and thus as long as the subject is supplied with the feed composition for the purpose of improving its immunity through inducing interferon-β expression, the feed composition can be applied to any type of subjects. For example, the feed composition can be applied to the subjects including non-human animals such as a monkey, dog, cat, rabbit, guinea pig, rat, mouse, cow, sheep, pig, and goat; birds; and fish.

The pharmaceutical composition of the present invention can be applied to any type of subjects, as long as the purpose of administration is to enhance the immunity in the subject through inducing interferon-β expression. Examples of such subjects include non-human animals such as a monkey, dog, cat, rabbit, guinea pig, rat, mouse, cow, sheep, pig, and goat; birds; and fish.

As another aspect, the present invention relates to an over-the-counter (OTC) drug composition comprising the composition for enhancing immunity. The OTC drug composition can be prepared in the form of soap, cosmetics, wet tissue, tissue paper, shampoo, skin cream, face cream, toothpaste, lipstick, perfume, make-up, foundation, blush, mascara, eye shadow, sunscreen lotion, hair products, air freshener, gel, or cleansing gel, but is not limited thereto.

Other substances other than any one of the compounds represented by Formulas 1 to 8, pharmaceutically acceptable salt thereof, or *S. flavescens* extract comprising any one of the compounds or fractions thereof can be selected and added to the composition according to the formulation of OCT drugs or the purpose of its usage. The amount of active ingredients to add can be properly determined according to the intended purpose of the OTC drugs (prevention or alleviation). For example, the type of other substances may include a conventional supplemental agent such as a thickener, stabilizer, solublizing agent, vitamin, pigments, and flavoring; and a carrier.

The over-the-counter (OTC) drug composition of the present invention can be applied to any type of subjects, as long as the purpose of administration is to enhance the immunity in the subject through inducing interferon-β expression. Examples of such subjects include non-human animals such as a monkey, dog, cat, rabbit, guinea pig, rat, mouse, cow, sheep, pig, and goat; birds; and fish.

As another aspect, the present invention provides a food composition comprising the composition for enhancing immunity. The food composition of the present invention may contain a various type of nutrients, vitamins, electrolytes, artificial or natural flavoring agents, colorants, fillers (e.g., cheese and chocolate), pectic acid or salt thereof, alginic acid or salt thereof, organic acids, protective colloidal tackifiers, pH adjusters, stabilizers, preservatives, glycerin, alcohol, carbonating agents used in carbonated drinks, and such. Additionally, the food composition of the present invention may contain a natural fruit juice and extracts for preparing a fruit juice and vegetable juice beverage. These components may be used alone or in combination. These substances can be used alone or as a mixture. Furthermore, the food composition can be in any one of the forms including meats, sausages, bread, chocolate, candies, snack, confectionery, pizza, noodles, gums, dairy products including ice cream, soup, beverage, tea, drinks, alcoholic beverages, and multi-vitamin preparations.

The food composition of the present invention can be applied to any type of subjects, as long as the purpose of administration is to enhance the immunity in the subject through inducing interferon-β expression. Examples of such subjects include non-human animals such as a monkey, dog, cat, rabbit, guinea pig, rat, mouse, cow, sheep, pig, and goat; birds; and fish.

The composition for enhancing immunity of the present invention can be used for treating diseases that can be prevented or treated by increasing the expression of interferon-β.

Figures 3, 4A:
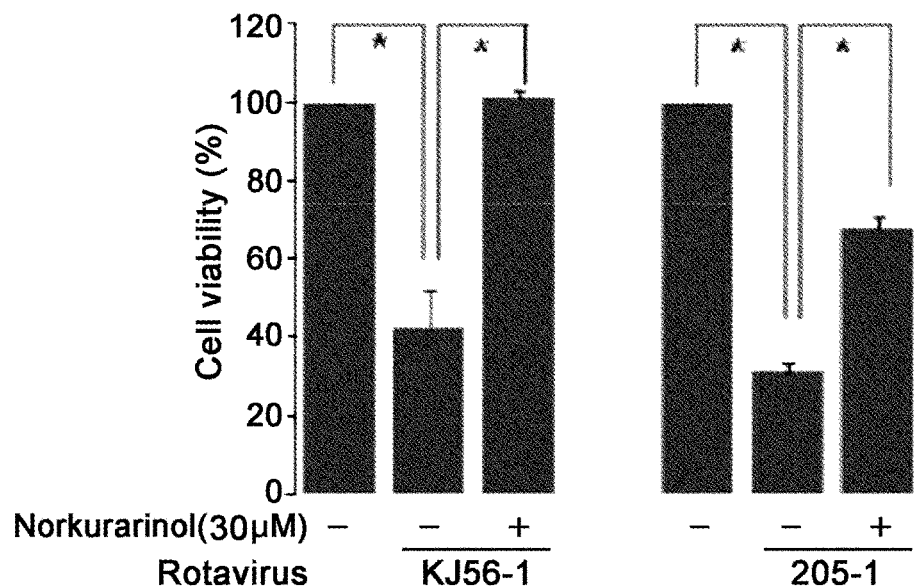
FIG. 3 shows the effects of the compound of Formula on the proliferation of TF-104 cells which are previously infected by bovine rotavirus KJ56-1 or porcine rotavirus 205-1.
FIG. 4a shows the inhibitory effect of the compounds represented by Formulas 2 to 8 on proliferation of TF-104 cells infected by rotavirus KJ56-1.

Interferon-β has an antiviral activity and thus the diseases that can be prevented or treated by increasing the expression of interferon-β include viral diseases. The present inventors have specifically confirmed that the compounds represented by Formulas 1 to 8 of the present invention have a high inhibitory effect against proliferation of rotavirus (FIGS. 3 and 4a). Therefore, the composition for enhancing immunity through inducing the expression of interferon-β can be used as a feed additive and feed composition comprising the same, food composition, and OTC drug composition for the prevention or treatment of the diseases including viral diseases that can be prevented or treated by increasing the expression of interferon-β, and it can also be used as a pharmaceutical composition for the prevention or treatment of the diseases that can be prevented or treated by increasing the expression of interferon-β.

Furthermore, the composition for enhancing the immunity in the present invention can be administered to the subject suspected to have or infected with the diseases in order to prevent, alleviate, or treat the diseases.

If a substance capable of suppressing the viral proliferation without having toxicity in body is properly mixed with the substance inducing the expression of interferon-β, the diseases that are preventable or treatable by increasing the expression of interferon-β can be prevented or treated, and in other words, it can suppress the viral proliferation and extensive inflammatory response caused by viral infection simultaneously, thereby providing a synergic effect for inhibiting the development of viral infection disease. For example, if *stevia rebaudiana* extract or stevioside is added along with the composition of the present invention, the antiviral effects of the composition will be enhanced, and thus it can be useful for the prevention or treatment of the viral infection diseases.

As another aspect, the present invention provides a feed additive and feed composition comprising the same that comprise the composition for enhancing immunity through induction of the expression of interferon-β as an active ingredient for prevention or alleviation of more than one of the diseases selected from the group consisting of infectious diseases including rotavirus, porcine reproductive and respiratory syndrome virus, Coxsackievirus, Colorado tick fever virus, reovirus, human immunodeficiency virus, and hepatitis B and C; inflammation including atopic dermatitis, psoriasis, Anaphylaxis and dermatitis, and IgE-mediated(type) hyperergia; Ocular disease including diabetic retinopathy, retinitis, maculopathy, uveitis, and conjunctivitis; angiosis including stroke, vessel disease, myocardial infarction, unstable angina, angiitis, vascular sclerosis, angiostenosis, Wegener's granulomatosis, Churg-Strauss angiiti Henoch-Schonlein purpura, Kawasaki disease, and giant cell arteritis; and ankylosing spondylitis, osteoporosis, allergy, diabete mellitus, diabetic nephropathy, acute childhood diabetes, Addison's disease, Goodpasture's sydrome, IgA nephropathy, Bright's disease, nephritis, sjogren's syndrome, auto-immune pancreatitis, periodontal disease, chronic obstructive pulmonary disease, acute leukemia-mediated pulmonary damage, asthma, graft versus host disease, chronic pelvic inflammatory disease, endometritis, rhinitis, metastasis, transplant rejection, stroke, encephalitis, meningitis, AIDS-dementia, fibrosis, adhesion formation, chronic hepatitis, osteosarcoma, basal cell carcinoma, cervix dysplasia, neuroglioma, acute myelogenous leukemia, multiple myeloma, Hodgkin's disease, breast cancer, melanoma, papilloma virus, viral hepatitis, herpes genitalis, herpes zoster, vesicular keratitis, herpes simplex, viral encephalitis, giant cell pneumonia, viral coryza, Chronic hepatitis C, Alzheimer's disease, Creutzfeld-Jakob disease, Gerstmann-Straussler-Scheinker Disease, severe acute respiratory syndrome, stroke, temporary ischaemic attacks and chronic prostatitis.

As another aspect, the present invention provides a feed additive and food composition comprising the same that comprise the composition for enhancing immunity through induction of the expression of interferon-β as an active ingredient for prevention or alleviation of more than one of the diseases selected from the group consisting of infectious diseases including rotavirus, porcine reproductive and respiratory syndrome virus, Coxsackievirus, Colorado tick fever virus, reovirus, human immunodeficiency virus, and hepatitis B and C; inflammation including atopic dermatitis, psoriasis, Anaphylaxis and dermatitis, and IgE-mediated(type) hyperergia; Ocular disease including diabetic retinopathy, retinitis, maculopathy, uveitis, and conjunctivitis; angiosis including stroke, vessel disease, myocardial infarction, unstable angina, angiitis, vascular sclerosis, angiostenosis, Wegener's granulomatosis, Churg-Strauss angiitis, Henoch-Schonlein purpura, Kawasaki disease, and giant cell arteritis; and ankylosing spondylitis, osteoporosis, allergy, diabete mellitus, diabetic nephropathy, acute childhood diabetes, Addison's disease, Goodpasture's sydrome, IgA nephropathy, Bright's disease, nephritis, sjogren's syndrome, auto-immune pancreatitis, periodontal disease, chronic obstructive pulmonary disease, acute leukemia-mediated pulmonary damage, asthma, graft versus host disease, chronic pelvic inflammatory disease, endometritis, rhinitis, metastasis, transplant rejection, stroke, encephalitis, meningitis, AIDS-dementia, fibrosis, adhesion formation, chronic hepatitis, osteosarcoma, basal cell carcinoma, cervix dysplasia, neuroglioma, acute myelogenous leukemia, multiple myeloma, Hodgkin's disease, breast cancer, melanoma, papilloma virus, viral hepatitis, herpes genitalis, herpes zoster, vesicular keratitis, herpes simplex, viral encephalitis, giant cell pneumonia, viral coryza, Chronic hepatitis C, Alzheimer's disease, Creutzfeld-Jakob disease, Gerstmann-Straussler-Scheinker Disease, severe acute respiratory syndrome, stroke, temporary ischaemic attacks and chronic prostatitis.

As another aspect, the present invention provides a feed additive, and OTC composition comprising the same that comprise the composition for enhancing immunity through induction of the expression of interferon-β as an active ingredient for prevention or alleviation of more than one of the diseases selected from the group consisting of infectious diseases including rotavirus, porcine reproductive and respiratory syndrome virus, Coxsackievirus, Colorado tick fever virus, reovirus, human immunodeficiency virus, and hepatitis B and C; inflammation including atopic dermatitis, psoriasis, Anaphylaxis and dermatitis, and IgE-mediated(type) hyperergia; Ocular disease including diabetic retinopathy, retinitis, maculopathy, uveitis, and conjunctivitis; angiosis including stroke, vessel disease, myocardial infarction, unstable angina, angiitis, vascular sclerosis, angiostenosis, Wegener's granulomatosis, Churg-Strauss angiitis, Henoch-Schonlein purpura, Kawasaki disease, and giant cell arteritis; and ankylosing spondylitis, osteoporosis, allergy, diabete mellitus, diabetic nephropathy, acute childhood diabetes, Addison's disease, Goodpasture's sydrome, IgA nephropathy, Bright's disease, nephritis, sjogren's syndrome, auto-immune pancreatitis, periodontal disease, chronic obstructive pulmonary disease, acute leukemia-mediated pulmonary damage, asthma, graft versus host disease, chronic pelvic inflammatory disease, endometritis, rhinitis, metastasis, transplant rejection, stroke, encephalitis, meningitis, AIDS-dementia, fibrosis, adhesion formation, chronic hepatitis, osteosarcoma, basal cell carcinoma, cervix dysplasia, neuroglioma, acute myelogenous leukemia, multiple myeloma, Hodgkin's disease, breast cancer, melanoma, papilloma virus, viral hepatitis, herpes genitalis, herpes zoster, vesicular keratitis, herpes simplex, viral encephalitis, giant cell pneumonia, viral coryza, Chronic hepatitis C, Alzheimer's disease, Creutzfeld-Jakob disease, Gerstmann-Straussler-Scheinker Disease, severe acute respiratory syndrome, stroke, temporary ischaemic attacks and chronic prostatitis.

As used herein, the term "prevention" refers to all actions that inhibit or delay the onset of the diseases that can be prevented or treated by increasing the expression of interferon-β, through inducing the expression of interferon-β by using the composition comprising any one of the compounds represented by Formulas 1 to 8 or a pharmaceutically acceptable salt thereof, or *Sophora flavescens* extract comprising any one of the compounds or fractions thereof as an active ingredient.

As used herein, the term "alleviation" refers to all actions that alleviate or beneficially change the symptoms of the subjects who are suspected of or acquire the diseases that can be prevented n treated by increasing the expression of interferon-β. The alleviation of diseases is done by inducing the expression of interferon-β through administration of the feed additive, feed composition, food composition, or OCT drug composition which comprises any one of the compounds represented by Formulas 1 to 8, pharmaceutically acceptable salt thereof, or *Sophora flavescens* extract comprising any one of the compounds or fractions thereof as an active ingredient.

As another aspect, the present invention provides a pharmaceutical composition that comprises the composition for enhancing immunity through induction of the expression of interferon-β as an active ingredient for prevention or alleviation of more than one of the diseases selected from the group consisting of infectious diseases including rotavirus, porcine reproductive and respiratory syndrome virus, Coxsackievirus, Colorado tick fever virus, reovirus, human immunodeficiency virus, and hepatitis B and C; inflammation including atopic dermatitis, psoriasis, Anaphylaxis and dermatitis, and IgE-mediated(type) hyperergia; Ocular disease including diabetic retinopathy, retinitis, maculopathy, uveitis, and conjunctivitis; angiosis including stroke, vessel disease, myocardial infarction, unstable angina, angiitis, vascular sclerosis, angiostenosis, Wegener's granulomatosis, Churg-Strauss angiitis, Henoch-Schonlein purpura, Kawasaki disease, and giant cell arteritis; and ankylosing spondylitis, osteoporosis, allergy, diabete mellitus, diabetic nephropathy, acute childhood diabetes, Addison's disease, Goodpasture's sydrome, IgA nephropathy, Bright's disease, nephritis, sjogren's syndrome, auto-immune pancreatitis, periodontal disease, chronic obstructive pulmonary disease, acute leukemia-mediated pulmonary damage, asthma, graft versus host disease, chronic pelvic inflammatory disease, endometritis, rhinitis, metastasis, transplant rejection, stroke, encephalitis, meningitis, AIDS-dementia, fibrosis, adhesion formation, chronic hepatitis, osteosarcoma, basal cell carcinoma, cervix dysplasia, neuroglioma, acute myelogenous leukemia, multiple myeloma, Hodgkin's disease, breast cancer, melanoma, papilloma virus, viral hepatitis, herpes genitalis, herpes zoster, vesicular keratitis, herpes simplex, viral encephalitis, giant cell pneumonia, viral coryza, Chronic hepatitis C, Alzheimer's disease, Creutzfeld-Jakob disease, Gerstmann-Straussler-Scheinker Disease, severe acute respiratory syndrome, stroke, temporary ischaemic attacks and chronic prostatitis.

As used herein, the term "treatment" refers to all actions that treat or beneficially change the conditions of subjects who are suspected of having or have already acquired the disease that can be prevented or treated by increasing the expression of interferon-β. The treatment of disease is done by inducing the expression of interferon-β through administration of the feed additive, feed composition, food composition, or OCT drug composition which comprises any one of the compounds represented by Formulas 1 to 8, pharmaceutically acceptable salt thereof, or *Sophora flavescens* extract comprising any one of the compounds or fractions thereof as an active ingredient.

As another aspect, the present invention provides a method for enhancing immunity of an immunodepressed subject, comprising the step of administrating the composition for enhancing immunity to the immunodepressed subject.

As another aspect, the present invention provides a method for treating rotavirus-mediated diseases, comprising the step of administrating the composition for enhancing immunity to the rotavirus-infected subject.

The rotavirus-mediated disease includes diarrhea occurring in young animals (cow, pig, dog, and goat) and in infants.

MODE FOR INVENTION

Hereinafter, the present invention is described in more detail with reference to Examples. However, these Examples are for illustrative purposes only, and the invention is not intended to be limited by these Examples.

Example 1

Extraction, Separation, and Purification of the Flavanone-Type Compounds Represented by Formulas 1 to 8 from *Sophora flavescens*

Example 1-1

Preparation of *Sophora flavescens* Extract

*S. flavescens* was washed with water, dried under shade, and ground into powder by using a Waring blender. The 5.5 kg of the ground *S. flavescens* was added to 20 L of ethanol and maceration extraction was performed for 3 days at a room temperate. The extract was filtered with pressure through a filter paper (Whatman, U.S.A.), and then ethanol solvent was removed from the filtered extract by using a rotary vacuum evaporator at a room temperature. The 450 g of *S. flavescens* crude extract was obtained.

In order to isolate and purify an active substance from the crude extract, the *S. flavescens* crude extract was suspended in 1 L of water and fractionated by mixing it with the equal amount of chloroform, and this process was repeated 4 times. At the end, 1 L of water-soluble fraction and 4 L of chloroform-soluble fraction were obtained, and then the chloroform-soluble fraction was concentrated with pressure to obtain 50 g of chloroform-soluble extract.

Example 1-2

Separation and Purification of Chloroform Layer

The 50 g of chloroform-soluble extract obtained in Example 1-1 was run through a silica-gel column chromatography using a step gradient solvent system with hexane:ethyl acetate=(100/0 to 0/100, v/v) for isolation of the active fractions.

Among the active fractions, Fraction No. 8 (1.6 g) with the highest inhibition activity was further run through a silica-gel column chromatography while successively increasing the ratio of acetone in a mixed solvent of hexane:acetone. Among these fractions, the fractions with the highest inhibition activity were collected and subsequently run through the silica-gel column chromatography using a mixed solvent of hexane:acetone. After repeating this step several times, Compound 1 (100 mg) was obtained in the form of a yellow powder substance. Likewise, Fraction No. 3 (3 g) was run through a silica-gel column chromatography while successively increasing the ratio of ethyl acetate and acetone in a mixed solvent of hexane:ethyl acetate and hexane:acetone respectively, and then Compound 2 (500 mg) and Compound 6 (250 mg) were obtained respectively in the form of yellow powder substances. Fraction No. 4 (1.4 g) was run through the silica-gel column chromatography using a mixed solvent of hexane:acetone and Compound 5 (570 mg) was obtained in the form of white powdery substance. Fraction No. 5 (5 g) was run through the silica-gel column chromatography using a mixed solvent of hexane:ethyl acetate and hexane:acetone, yielding Compound 3 (530 mg) in a yellow powder form and Compound 7 (100 mg) in a white powder form. Fraction No. 6 (2.3 g) was run through the silica-gel column chromatography repeatedly using a mixed solvent of hexane:acetone, yielding Compound 4 (40 mg) in a white powder form and Compound 8 (200 mg) in a yellow powder form.

Example 2

Analysis of Physicochemical Properties of the Compounds Represented by Formulas 1 to 8

The compound of Formula 1 appeared as yellow powder substance. In NMR analysis, Compound 1 showed one $sp^2$ methylene group, four $sp^3$ methylene groups, three methyl groups, six methine groups and ten tertiary carbons on DEPT spectrum of $^{13}$C-NMR, and twenty five protons on $^1$H-NMR spectrum. In a mass spectrum, the compound of Formula 1 showed the molecular ion (M+) peak at m/z=442. Based on the $^1$H-NMR, $^{13}$C-NMR, and mass spectrum data, the molecular formula of the compound of Formula 1 was determined to be $C_{25}H_{30}O_7$. Furthermore, from this molecular formula, it was identified that the degree of unsaturation of the compound of Formula 1 is 11 and that the compound has five hydroxyl groups. Using $^1$H-NMR data, it was identified that Compound 1 has a typical flavanone structure based on the presence of three double peaks in ABX system i.e., H-3a ($\delta_H$ 3.08 ppm), H-3b ($\delta_H$ 3.13 ppm), and H-2 ($\delta_H$ 5.68 ppm). In the $^1$H-$^1$H COSY spectrum, cross peaks were observed from H-1" ($\delta_H$ 2.77 ppm) to H-10" ($\delta_H$ 4.61 ppm) and also from H-4" to H-7"/H-6". Also, allylic coupling (H-2"→H-10") was observed in the $^1$H-NMR. Based on the above results, it was identified that Compound 1 has a lavandulyl group. The cross peak of C-8 ($\delta_C$ 108.3 ppm) and H-1" ($\delta_H$ 2.77 ppm) observed in HMBC spectrum demonstrates that a lavandulyl group is positioned at C-8. Overall, the structure of the compound of Formula 1 was determined as 5,7,2',4'-trihydroxy-8-(5-hydroxy-2-isoprenyl-5-methyl-hexyl-)flavanone, that is, norkurarinol.

Compound 2 is a yellow powder substance and showed one sp$^2$ methylene group, three sp$^3$ methylene groups, three methyl groups, seven methine groups and ten tertiary carbons in the DEPT spectrum of $^{13}$C-NMR, and twenty five protons in the $^1$H-NMR spectrum. In a mass spectrum, Compound 2 showed the molecular ion (M+) peak at m/z=424. Using the $^1$H-NMR, $^{13}$C-NMR, and mass spectrum data, the molecular formula of Compound 2 was determined to be $C_{25}H_{28}O_6$. Also, it was identified that Compound 2 has four hydroxyl groups. Furthermore, through $^1$H-NMR data it was confirmed that Compound 2 has a typical flavanone structure based on the presence of three double peaks in ABX system i.e., H-3a ($\delta_H$ 2.73 ppm), H-3b ($\delta_H$ 2.97 ppm) and H-2 ($\delta_H$ 5.56 ppm). In the $^1$H-$^1$H COSY spectrum, cross peaks were observed from H-1" ($\delta_H$ 2.85 ppm) to H-10" ($\delta_H$ 4.55 ppm) and also from H-4" to H-7"/H-6". Also, in the $^1$H-NMR, allylic couplings (H-4"→H-7") and (H-2"→H-10") were observed. Based on the above results, the presence of lavandulyl group in Compound 2 was confirmed. The cross peak of C-8 ($\delta_c$ 109.1 ppm) and H-1" ($\delta_H$ 2.85 ppm) in the HMBC spectrum suggests that the lavandulyl group is positioned at C-8. In overall, the structure of Compound 2 was determined as 5,7,2',4'-tetrahydroxy-8-lavandulylflavanone, that is, sophoraflavanone.

Compound 3 is a yellow powder substance, and showed the molecular ion (M+) peak at m/z=438 in the mass spectrum. Using the $^1$H-NMR, $^{13}$C-NMR, and mass spectrum data, the molecular formula of Compound 3 was deduced to $C_{26}H_{30}O_6$, and also it was identified that Compound 3 is a similar type of chemical compound as Compound 2 having a lavandulyl group at C-8. Compound 3 had a methoxy group instead of hydroxyl group at C-5. In overall, the structure of Compound 3 was determined as 5-methoxy-7,2',4'-trihydroxy-8-lavandulylflavanone, that is, kurarinone.

Compound 4 is a white powder substance, and showed a molecular ion (M+) peak at m/z=354 in the mass spectrum. Using the $^1$H-NMR, $^{13}$C-NMR, and mass spectrum data, the molecular formula of Compound 4 was deduced to $C_{21}H_{22}O_5$, and also it was confirmed that Compound 4 has a methoxy group instead of hydroxyl group at C-5, as in Compound 3. Also, Compound 4 has a prenyl group at C-8, instead of a lavandulyl group. In overall, the structure of Compound 4 was determined as 5-methoxy-7,4'-dihydroxy-8-prenylflavanone, that is, isoxanthohumol.

Compound 5 is a yellow powder substance, and showed a molecular ion (M+) peak at m/z=438 in the mass spectrum. Based on the $^1$H-NMR, $^{13}$C-NMR, and mass spectrum data, the molecular formula of Compound 5 was deduced to $C_{26}H_{30}O_6$, and it was confirmed that Compound 5 has a lavandulyl group at C-8 as similar to Compound 2. Compound 5 has a methoxy group at C-2 instead of hydroxyl group. In overall, the structure of Compound 5 was determined as 2'-methoxy-5,7,4'-trihydroxy-8-lavandulylflavanone, that is, leachianone A.

Compound 6 is a yellow powder substance, and showed a molecular ion (M+) peak at m/z=438 in the mass spectrum. Based on the $^1$H-NMR, $^{13}$C-NMR, and mass spectrum data, the molecular formula of Compound 3 was deduced to $C_{25}H_{28}O_5$, and also it was identified that Compound 6 is a similar type of chemical compound as Compound 2, having a lavandulyl group at C-8. Unlike Compound 2, however, Compound 6 does not have a hydroxyl group at C-4'. In overall, the structure of Compound 6 was determined as 5,7,2'-trihydroxy-8-lavandulylflavanone, that is, kushenol A.

Compound 7 is a yellow powder substance, and showed a molecular ion (M+) peak at m/z=426 in the mass spectrum. Based on the $^1$H-NMR, $^{13}$C-NMR, and mass spectrum data, the molecular formula of Compound 7 was deduced to $C_{25}H_{30}O_6$, and also it was identified that Compound 7 has a similar chemical structure as Compound 6. However, no double bonding was observed between C-4" and C-5" in Compound 7, and there is one additional hydroxyl group at C-5". In overall, the structure of Compound 7 was determined as 5,7,2'-trihydroxy-8-(5-hydroxy-2-isoprenyl-5-methyl-hexyl)-flava-none, that is, kushenol T.

Compound 8 is a yellow powder substance, and showed a molecular ion (M+) peak at m/z=452 in the mass spectrum. Based on the $^1$H-NMR, $^{13}$C-NMR, and mass spectrum data, the molecular formula of Compound 8 was deduced to $C_{27}H_{32}O_6$, and also it was identified that Compound 8 is a similar type of chemical compound as Compound 2 having a lavandulyl group at C-8. Compound 8 has a methoxy group at C-5 and C-2 instead of hydroxy group. In overall, the structure of Compound 8 was determined as 5,2'-methoxy-7,4'-dihydroxy-8-lavandulylflavanone, that is, 2'-methoxykurarinonedm.

The physiochemical properties of the compounds represented by Formulas 1 to 8 are as follows.

[Formula 1]

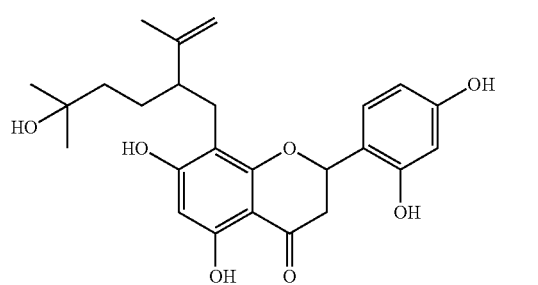

(1) physical form: yellow powder
(2) Molecular formula and molecular weight: $C_{25}H_{30}O_7$, 442
(3) Proton nuclear magnetic resonance (1H NMR) spectrum [500 MHz, acetone-d$_6$, d(ppm)]: 7.39 (1H, d, J=8.31 Hz, H-6'), 6.49 (1H, m, H-3'), 6.46 (1H, m, H-5'), 6.02 (1H, s, H-6), 5.68 (1H, dd, J=13.2, 2.8 Hz, H-2), 4.61 (2H, m, H-10"), 3.13 (1H, m, H-3a), 3.08 (1H, m, H-3b), 2.77 (2H, dd, J=17.1, 2.9 Hz, H-1"), 2.46 (1H, m, H-2"), 1.66 (3H, s, H-9"), 1.39 (2H, m, H-3"), 1.26 (2H, m, H-4"), 1.11 (3H, s, H-6"), 1.10 (3H, s, H-7")
(4) Carbon nuclear magnetic resonance (C-13 NMR) spectrum [125 MHz, acetone-d$_6$, d(ppm)]: 198.6 (C-4), 165.8 (C-7), 163.4 (C-5), 162.5 (C-9), 159.8 (C-4'), 156.7 (C-2'), 149.6 (C-8"), 129.1 (C-6'), 118.3 (C-10), 111.8 (C-10"), 108.4 (C-1'), 108.3 (C-8), 104.0 (C-3'), 103.7 (C-5'), 96.7 (C-6), 75.8 (C-2), 70.9 (C-5"), 48.6 (C-2"), 43.0 (C-3), 43.0 (C-1"), 30.1 (C-6"), 29.9 (C-7"), 28.6 (C-3"), 28.1 (C-4"), 19.1 (C-9")

111.6 (C-10"), 110.0 (C-8), 108.1 (C-3'), 106.2 (C-10), 103.8 (C-5'), 93.7 (C-6), 75.9 (C-2), 56.3 (C-11"), 48.6 (C-2"), 46.0 (C-3), 32.8 (C-3"), 28.6 (C-1"), 26.3 (C-7"), 19.6 (C-9"), 18.2 (C-6")

[Formula 2]

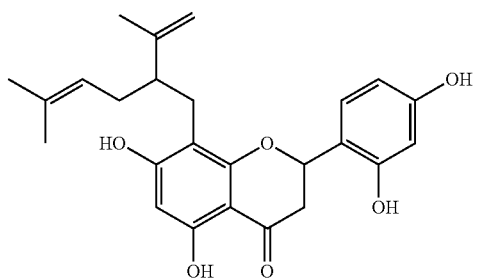

(1) Physical form: yellow powder
(2) Molecular formula and molecular weight: $C_{25}H_{28}O_6$, 424
(3) Proton nuclear magnetic resonance ($^1$H NMR) spectrum [500 MHz, $CD_3OD$, d(ppm)]: 7.30 (1H, d, J=8.2 Hz, H-6'), 6.37 (1H, d, J=2.3 Hz, H-3'), 6.35 (1H, m, H-5'), 5.92 (1H, s, H-6), 5.56 (1H, dd, J=13.2, 2.7 Hz, H-2), 4.90 (1H, m, H-4"), 4.55 (2H, m, H-10"), 2.97 (1H, dd, J=17.1, 13.2 Hz, H-3), 2.85 (2H, m, H-1"), 2.73 (1H, dd, J=17.1, 2.8 Hz, H-3), 2.47 (1H, m, H-2"), 2.00 (2H, m, H-3"), 1.63 (3H, s, H-7"), 1.56 (3H, s, H-9"), 1.48 (3H, s, H-6")
(4) Carbon nuclear magnetic resonance (C-13 NMR) spectrum [125 MHz, $CD_3OD$, d(ppm)]: 199.4 (C-4), 166.9 (C-7), 163.6 (C-5), 163.0 (C-9), 159.9 (C-4'), 157.1 (C-2'), 150.1 (C-8"), 132.5 (C-5"), 129.1 (C-6'), 125.2 (C-4"), 118.8 (C-1'), 111.6 (C-10"), 109.1 (C-8), 103.8 (C-5'), 96.7 (C-6), 76.2 (C-2), 48.7 (C-2"), 43.7 (C-3), 32.8 (C-3"), 28.4 (C-1"), 26.3 (C-7"), 19.6 (C-9"), 18.3 (C-6")

[Formula 4]

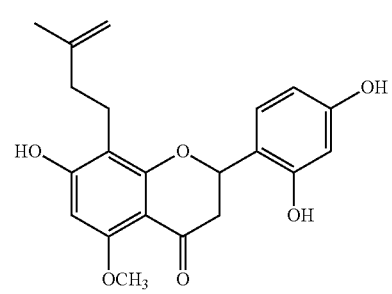

(1) Physical form: white powder
(2) Molecular formula and molecular weight: $C_{21}H_{22}O_5$, 354
(3) Proton nuclear magnetic resonance (1H NMR) spectrum [500 MHz, $CD_3OD$, d(ppm)]: 7.30 (1H, dd, J=6.7, 1.7 Hz, H-2', H-6'), 6.81 (1H, dd, J=6.7, 2.0 Hz, H-3', H-5'), 6.11 (1H, s, H-6), 5.26 (1H, dd, J=12.8, 3.1 Hz, H-2), 5.13 (1H, m, H-2"), 3.79 (3H, s, H-6"), 3.20 (2H, m, H-1"), 2.96 (1H, dd, J=16.6, 12.8 Hz, H-3), 2.65 (1H, dd, J=16.6, 3.1 Hz, H-3), 1.61 (3H, s, H-5"), 1.56 (3H, s, H-4")
(4) Carbon nuclear magnetic resonance (C-13 NMR) spectrum [125 MHz, $CD_3OD$, d(ppm)]: 193.3 (C-4), 164.7 (C-7), 164.2 (C-9), 162.2 (C-5), 159.2 (C-4'), 132.1 (C-1'), 132.0 (C-3"), 129.3 (C-6'), 129.1 (C-2'), 124.3 (C-2"), 116.7 (0-3'), 116.5 (0-5'), 110.4 (C-8), 106.3 (C-10), 93.9 (C-6), 80.4 (C-2), 56.4 (C-6"), 46.6 (C-3), 26.4 (C-5"), 23.1 (C-1"), 18.3 (C-4")

[Formula 3]

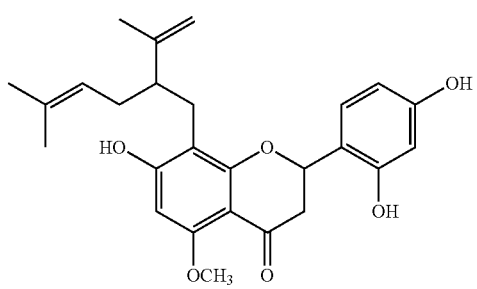

(1) Physical form: yellow powder
(2) Molecular formula and molecular weight: $C_{26}H_{30}O_6$, 438
(3) Proton nuclear magnetic resonance ($^1$H NMR) spectrum [500 MHz, $CD_3OD$, d(ppm)]: 7.30 (1H, d, J=8.2 Hz, H-6'), 6.36 (1H, d, J=2.3 Hz, H-3'), 6.34 (1H, m, H-5'), 6.10 (1H, s, H-8), 5.54 (1H, dd, J=13.2, 2.8 Hz, H-2), 4.96 (1H, m, H-4"), 4.57 (2H, m, H-10"), 3.80 (3H, s, H-11"), 2.87 (1H, dd, J=16.7, 2.8 Hz, H-3), 2.70 (1H, dd, J=16.7, 13.2 Hz, H-3), 2.62 (2H, m, H-1"), 2.49 (1H, m, H-2"), 2.00 (2H, m, H-3"), 1.63 (3H, s, H-9"), 1.56 (3H, s, H-7"), 1.45 (3H, s, H-6")
(4) Carbon nuclear magnetic resonance (C-13 NMR) spectrum [125 MHz, $CD_3OD$, d(ppm)]: 194.3 (C-4), 165.3 (C-7), 165.1 (C-9), 162.3 (C-5), 159.9 (C-4'), 157.1 (C-2'), 150.2 (C-8"), 132.4 (C-5"), 128.9 (C-6'), 125.2 (C-4"), 118.9 (C-1'),

[Formula 5]

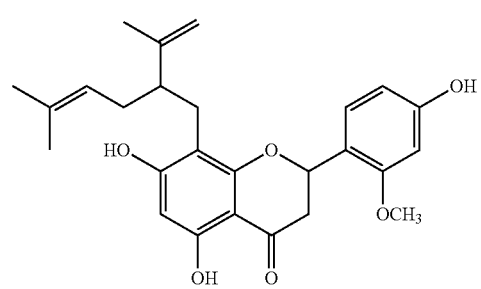

(1) Physical form: yellow powder
(2) Molecular formula and molecular weight: $C_{26}H_{30}O_6$, 438
(3) Proton nuclear magnetic resonance (1H NMR) spectrum [500 MHz, acetone-$d_6$, d(ppm)]: 7.30 (1H, d, J=8.4 Hz, H-6'), 6.42 (1H, d, J=2.7 Hz, H-3'), 6.39 (1H, m, H-5'), 5.88 (1H, s, H-6), (1H, dd, J=13.3, 2.7 Hz, H-2), 4.85 (1H, m, H-4"), 4.45 (2H, m, H-10"), 3.69 (3H, s, H-11"), 2.93 (1H, dd, J=13.3, 1.1 Hz, H-3), 2.90 (1H, dd, J=13.3, 1.1 Hz, H-3), 2.58 (2H, m, H-1"), 2.49 (1H, m, H-2"), 1.90 (2H, m, H-3"), 1.43 (3H, s, H-9"), 1.42 (3H, s, H-7"), 1.35 (3H, s, H-6")
(4) Carbon nuclear magnetic resonance (C-13 NMR) spectrum [125 MHz, acetone-$d_6$, d(ppm)]: 198.5 (C-4), 165.6 (C-7), 165.6 (C-9), 163.4 (C-5), 160.2 (C-4'), 159.0 (C-2'), 149.5 (C-8"), 132.0 (C-5"), 129.1 (C-6'), 124.8 (C-4"), 119.6 (C-1'), 111.5 (C-10), 103.6 (C-8), 103.5 (C-5'), 100.2

(C-10), 96.9 (C-3'), 93.7 (C-6), 75.4 (C-2), 56.2 (C-11"), 48.1 (C-2"), 43.2 (C-3), 32.3 (C-3"), 28.1 (C-1") 23.7 (C-7"), 19.5 (C-9"), 18.2 (C-6")

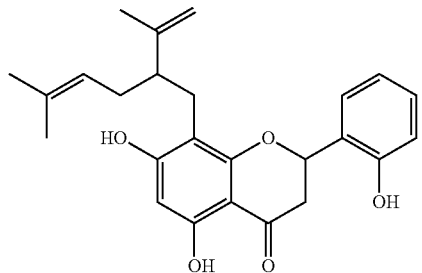

[Formula 6]

(1) Physical form: white powder
(2) Molecular formula and molecular weight: $C_{25}H_{28}O_5$, 408
(3) Proton nuclear magnetic resonance (1H NMR) spectrum [500 MHz, $CD_3OD$, d(ppm)]: 7.54 (1H, dd, J=7.6, 1.4 Hz, H-6'), 7.17 (1H, ddd, J=15.0, 7.6, 0.9 Hz, H-4'), 6.90 (1H, ddd, J=15.0, 7.6, 0.9 Hz, H-5'), 6.83 (1H, dd, J=8.1, 0.9 Hz, H-3'), 5.93 (1H, s, H-6), 5.63 (1H, dd, J=7.6, 1.4 Hz, H-2), 4.96 (1H, m, H-4"), 4.59 (2H, m, H-10"), 2.87 (2H, m, H-3), 2.61 (2H, m, H-1"), 2.48 (1H, m, H-2"), 2.00 (2H, m, H-3"), 1.64 (3H, s, H-9"), 1.55 (3H, s, H-7"), 1.46 (3H, s, H-6")
(4) Carbon nuclear magnetic resonance (C-13 NMR) spectrum [125 MHz, $CD_3OD$, d(ppm)]: 199.0 (C-4), 167.0 (C-7), 163.8 (C-9), 163.7 (C-5), 155.6 (C-2'), 150.1 (C-8"), 132.5 (C-5"), 130.6 (C-4'), 127.6 (C-1'), 127.6 (C-6'), 125.1 (C-4"), 121.0 (C-5'), 116.7 (C-3'), 111.6 (C-10"), 109.1 (C-8), 103.7 (C-10), 96.9 (C-6), 76.3 (C-2), 48.7 (C-2"), 43.6 (C-3), 32.7 (C-3"), 28.4 (C-1"), 26.2 (C-7"), 19.7 (C-9"), 18.2 (C-6")

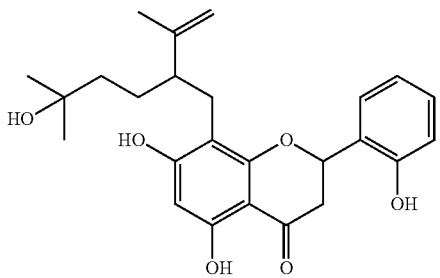

[Formula 7]

(1) Physical form: yellow powder
(2) Molecular formula and molecular weight: $C_{25}H_{30}O_6$, 426
(3) Proton nuclear magnetic resonance (1H NMR) spectrum [500 MHz, $CDCl_3$, d(ppm)]: 7.36 (1H, dd, J=7.6, 1.3 Hz, H-6'), 7.18 (1H, m, H-4'), 6.92 (1H, m, H-5'), 6.80 (1H, d, J=8.01 Hz, H-3'), 5.94 (1H, s, H-6), 5.61 (1H, dd, J=13.3, 2.7 Hz, H-2), 4.62 (2H, m, H-10"), 2.97 (1H, dd, J=17.2, 2.8 Hz, H-3), 2.83 (1H, dd, J=17.2, 13.4 Hz, H-3), 2.53 (2H, m, H-1"), 2.15 (2H, m, H-2"), 1.55 (3H, s, H-9"), 1.30 (2H, m, H-4"), 1.27 (2H, m, H-3"), 1.09 (3H, s, H-7"), 1.03 (3H, s, H-6")
(4) Carbon nuclear magnetic resonance (C-13 NMR) spectrum [125 MHz, $CDCl_3$, d(ppm)]: 197.6 (C-4), 164.5 (C-9), 162.2 (C-7), 160.9 (C-5), 153.6 (C-2'), 148.8 (C-8"), 130.1 (C-4'), 127.2 (C-6'), 125.6 (C-1'), 121.2 (C-5'), 117.1 (C-3'), 111.5 (C-10"), 108.2 (C-8), 103.3 (C-10), 96.9 (C-6), 76.1 (C-2), 72.5 (C-5"), 47.7 (C-2"), 42.1 (C-3), 41.2 (C-4"), 29.9 (C-7"), 28.8 (C-6"), 27.9 (C-1"), 19.5 (C-9")

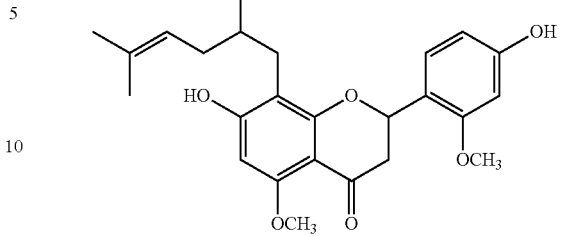

[Formula 8]

(1) Physical form: yellow powder
(2) Molecular formula and molecular weight: $C_{27}H_{32}O_6$, 452
(3) Proton nuclear magnetic resonance (1H NMR) spectrum [500 MHz, acetone-$d_6$, d(ppm)]: 7.30 (1H, d, J=8.2 Hz, H-6'), 6.49 (1H, m, H-3'), 6.36 (1H, d, J=2.3 Hz, H-3'), 6.34 (1H, m, H-5'), 6.10 (1H, s, H-6), 5.54 (1H, dd, J=13.2, 2.7 Hz, H-2), 4.96 (1H, m, H-4"), 4.57 (2H, m, H-10"), 3.80 (3H, s, H-12"), 3.79 (3H, s, H-11"), 2.87 (1H, dd, J=16.7, 3.2 Hz, H-3), 2.62 (2H, m, H-1"), 2.59 (1H, dd, J=6.7, 2.9 Hz, H-3), 2.49 (1H, m, H-2"), 2.00 (2H, m, H-3"), 1.63 (3H, s, H-9"), 1.56 (3H, s, H-7"), 1.45 (3H, s, H-6")
(4) Carbon nuclear magnetic resonance (C-13 NMR) spectrum [125 MHz, acetone-$d_6$, d(ppm)]: 194.3 (C-4), 165.3 (C-7), 165.1 (C-9), 162.3 (C-5), 159.9 (C-4'), 157.1 (C-2'), 150.2 (C-8"), 132.4 (C-5"), 128.9 (C-6'), 125.2 (C-4"), 118.9 (C-1'), 111.6 (C-10"), 110.0 (C-8), 108.1 (C-3'), 106.2 (C-10), 103.8 (C-5'), 93.7 (C-6), 75.9 (C-2), 56.3 (C-11"), 56.2 (C-12"), 48.6 (C-2"), 46.0 (C-3), 32.8 (C-3"), 28.6 (C-1"), 26.3 (C-7"), 19.6 (C-9"), 18.2 (C-6")

Example 3

Inductive Effect of S. flavescens Extract and Fractions Thereof on the Expression of IRF3 and Iterferon-β (IFN-β)

Interferon-β (IFN-β) whose expression is increased by phosphorylation of a transcription factor, interferon regulatory factor 3 (IRF3) has an antiviral activity through suppressing viral replication, and it has been increasingly used as an immunotherapy agent. In this light, the present inventors investigated the effects of the S. flavescens extract of the present invention on induction of the IRF3 and IFNβ expression under the following conditions.

First, in order to investigate the effects of the extract in activation of IRF3, THP-1 cells were prepared at a density of $1.5 \times 10^6$ cells/well and treated with 30 μg/ml of S. flavescens extract, 60 μg/ml of water fraction thereof, or 30 μg/ml of chloroform fraction thereof for 2 hours. After 2 hours of treatment with the extract and fractions thereof, the cells were put into tubes and pelleted down through centrifugation to remove culture media. Then the cell pellet was washed with PBS once and treated with cell lysis buffer to isolate total protein extracts, which were then subjected to western blot analysis. In this analysis, IRF3 protein level was measured.

The experimental results demonstrated a concentration-dependent increase in IRF3 activity in the group treated with S. flavescens extract and water fractions thereof, compared to the control group. Also, IRF3 activity was increased in the cells when treated with 30 μg/ml of chloroform fractions (FIG. 1a).

Subsequently, in order investigate the effects of *S. flavescens* extract and fractions thereof in IFN-β expression which is induced by IRF3 activation, following experiment was performed. The THP-1 cells were treated with 60 µg/ml of methanol extract of *S. flavescens*, 60 µg/ml of water fractions thereof, or 30 µg/ml of chloroform fraction thereof for 6 hours. After 6 hours of treatment, the cells were placed in tubes and pelleted down through centrifugation to remove cell media, which was then washed with PBS once and RNA was extracted from the washed cells by using RNeasy Mini Elute Cleanup kit. The concentration and purity of RNA extract was measured by using 2100 Bioanalyzer system (Agilent Technologies), and cDNA was synthesized from this RNA extract by using Taqman reverse transcription reagents kit (Applied Biosystems). The expression level of IFN-β was measured by running Real-time PCR using SYBR Green PCR master mix kit (Applied Biosystem).

As a result, it was confirmed that IFN-β expression was significantly increased in the group treated with methanol extract of *S. flavescens*, water fractions thereof, or chloroform fraction thereof, compared to the control group (FIG. 1b).

These results support that *S. flavescens* extract of the present invention and fractions thereof can induce the expression of IFN-β.

Example 4

Induction of IRF3 and IFN-β Expression by the Compounds Represented by Formulas 1 to 8

The signal transport pathway by TLR-3 activates not only NFkB and AP-1, but also IRF3 and thus induces the expression of IFNβ, thereby demonstrating antiviral activity. In this light, the present inventors investigated the effects of the compounds of the present invention in induction of IRF3 and IFN-β expression under the following conditions.

First, in order to investigate the effect of the extract in IRF3 activation, THP-1 cells were prepared at a density of $1.5 \times 10^6$ cells/well, and treated with the compound of Formula 1 at a concentration of 30 µM and 60 µM for 1 hour and then treated with 50 µg/ml of poly (I:C) for 3 hours. After 3 hours of treatment, the cells were placed in a tube and pelleted down through centrifugation to remove cell media, which was then washed with PBS once and mixed with NE-PER Nuclear extraction reagent (Thermo scientific) and cell lysis buffer to isolate nuclear extract and total protein extract. The isolated extracts were subject to western blot analysis.

As a result, it was found that the cell group treated with poly (I:C) showed an activation of IRF3. But interestingly, the group pre-treated with the compound of Formula 1 showed higher level of IRF3 activation compared to the group treated only with poly (I:C) (FIG. 2a). Furthermore, when the same experiment was performed to determine whether the cell treatment with only the compound of Formula 1 can increase the IRF3 activity, the concentration-dependent increased of IRF3 activity was observed when treated with the compound only (FIG. 2b). Also, the cell group pre-treated with Compounds 2 to 8 at 10 µM showed increased phosphorylation of IRF3 (FIG. 4b).

Subsequently, in order to investigate the effect of compound of Formula 1 in expression of IFN-β which is induced by IRF3 activation, the compound of Formula 1 was added to the cell group at a concentration of 10 µM, 30 µM, and 60 µM for 6 hours and then the expression level of IFNβ was measured.

The experimental results demonstrated a concentration-dependent increase of IFN-β expression by the compound of Formula 1 (FIG. 2c) and also increase of IFN-β expression by pre-treatment of cells with 10 µM Compounds 2 to 8 (FIG. 4c).

These results support that not only *S. flavescens* extract of the present invention and fractions thereof, but also the compounds of Formula 1 to 8 isolated therefrom can effectively induce the expression of IFN-β.

Example 5

Inhibitory Effect of the Compounds Represented by Formulas 1 to 8 Against Proliferation of Rotavirus In order to investigate the inhibitory effects of the above-disclosed compounds represented by Formulas 1 to 8 against proliferation of rotavirus, the following experiment was conducted using the fetal rhesus monkey kidney cell line TF-104. First, TF-104 cells ($1 \times 10^5$ cells/well) were treated with rotavirus KJ56-1 (bovine rotavirus, G8P[7]) with multiplicity of infection (MOI) of 0.01 for 1 hour. Then the supernatant was removed from the cell pellet, and the pelleted cells were added to EMEM medium mixed with 1 µg/ml of trypsin and compounds of Formulas 1 to 8 and cultured at 37° C. for 3 days.

As a result, it was confirmed that the proliferation of rotavirus KJ56-1 and rotavirus 205-1 was significantly inhibited by treatment with the compounds of Formula 1 at 30 µM (FIG. 3). Furthermore, pre-treatment with the compounds of Formulas 2 to 8 at a concentration of 10 µM also significantly inhibited the proliferation of rotavirus KJ56-1 (FIG. 4a).

These results support that the compounds of the present invention can effectively inhibit the proliferation of rotavirus.

Example 6

Inhibitory Effect of the Compound of Formula 1 Against the Expression of Inflammatory Factors Induced by Rotavirus Infection and Poly(I:C) Treatment In order to investigate the inhibitory effect of the compound of Formula 1 in inflammatory factor expression which is induced by poly (I:C) and rotavirus infection, the following experiment was performed using human peripheral blood monocytic cell lines THP-1 and TF-104.

In order to measure the inhibitory effect of the compound of Formula 1 against the induction of inflammatory factor expression by rotavirus infection, TF-104 cells were added to a 12 well-plate at a density of $5 \times 10^5$ cells/well. The compound of Formula 1 at a final concentration of 10 µM was added to the cell 1 hour prior to the rotavirus infection. Then, the cells were inoculated with 0.01 multiplicity of infection (MOI) rotavirus and incubated for 1 hour. After 1 hour, the supernatant of the cell culture was isolated in order to remove the remaining rotavirus that did not infect the cells. Subsequently, the EMEM medium mixed with 1 µg/ml of trypsin was added to the cells, which were then cultured at 37° C. for 48 hours. After removing the culture media, the cells were then washed once with PBS and collected into a tube by using a scraper. Then RNA extract was isolated by using RNeasy Mini Elute Cleanup kit. Subsequently, the effect of the compound of Formula 1 in inhibition of inflammatory factor induction as described above was measured.

Figure 7:
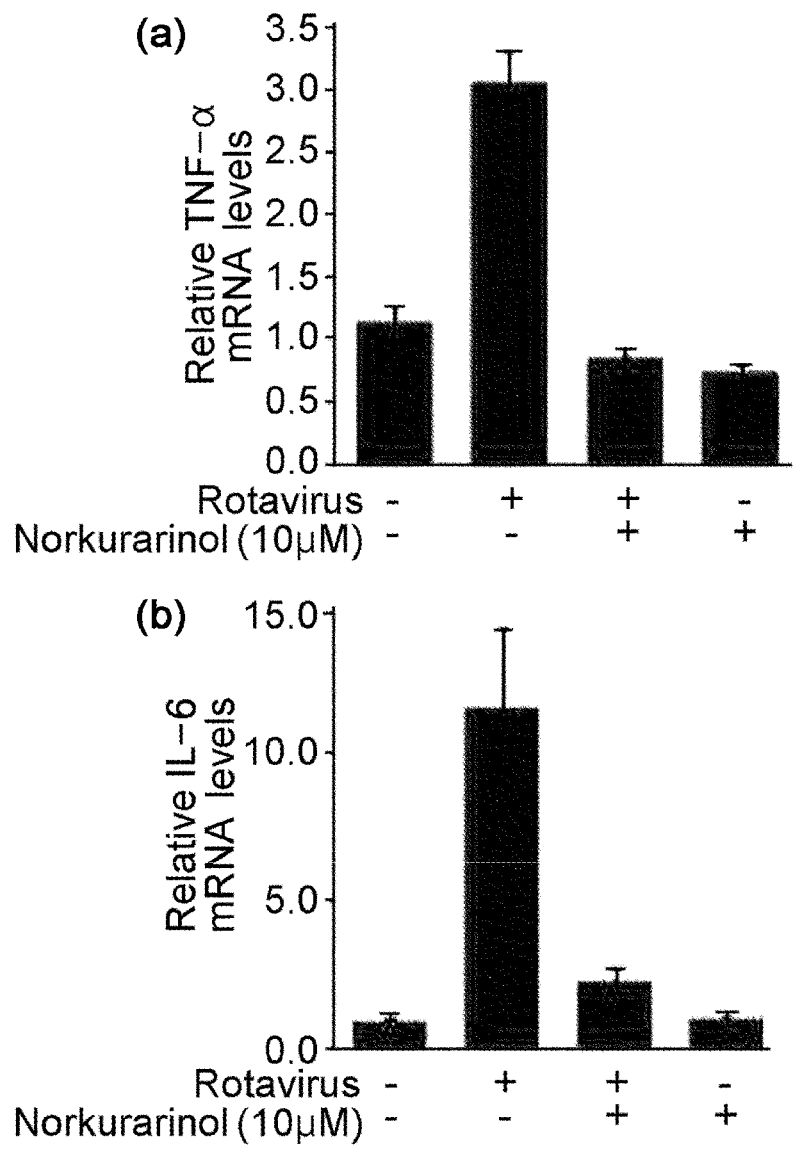
FIGS. 7a and 7b show the inhibitory effect of the compound of Formula 1 against the expression of TNF-α and IL-6 mRNAs which are the inflammatory cytokines induced by rotavirus infection in TF-104 cells.

As a result, compared to the control group uninfected with rotavirus, the cell group inoculated with rotavirus showed a significant increase in the expression of inflammatory cytokines TNF-a and IL-6. In contrast, the cell group pre-treated with the compound of Formula 1 (10 μM) prior to rotavirus infection showed a similar level of inflammatory cytokines as in the control group, thereby indicating that the present compounds can significantly inhibit the expression of inflammatory factors induced by rotavirus infection (FIG. 7).

Example 7

Changes in Distribution of TRIF-CFP In Vivo by the Compound of Formula 1

In order to monitor the changes in distribution of TRIF-CFP in vivo by the compound of Formula 1, THP-1 cells ($1\times10^6$ cells/well) were transfected with 0.5 μg of pcDNA3-TRIF-CFP plasmid by using Nucleofector kit V (Lonza, Switzerland) and cultured at 37° C. for 2 days. Then, the transfected cells were placed in 8-chamber slide coated with Poly-L-Lysine and treated with the compound of Formula 1 at 30 μM, and treated with 50 μg/ml of poly (I:C) for 1 hour. After removing the supernatant, the cells were washed with PBS three times, and fixed onto the slide by applying 200 μl of 4% paraformaldehyde and slowfade gold antifade reagent. Then the changes in the distribution of TRIF-CFP were monitored under carl zeins LSM 510 META confocal microscope.

Figure 8:
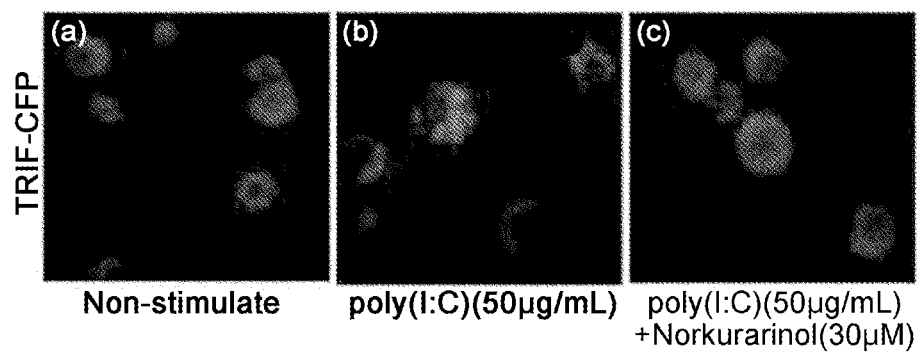
FIG. 8 shows the fluorescence microscopy images demonstrating the inhibitory effect of the compound of Formula 1 against the recruitment of TRIF-CFP in cytosol which is induced by poly(I:C) treatment in the THP-1 cells that are transiently transfected with TRIF-CFP DNA.

As a result, the control group untreated with poly (I:C) showed an even distribution of TRIF-CFP in the cytoplasm (FIG. 8(a)), whereas the cell group treated with poly (I:C) showed a concentrated distribution of TRIF-CFP (FIG. 8(b)). On the other hand, the cell group pre-treated with the compound of Formula 1 showed even distribution of TRIF-CFP in the cytoplasm as similar in the control group, thereby suggesting that the compound of Formula 1 can inhibit the concentrated distribution of TRIF-CFP induced by poly (I:C) (FIG. 8(c)).

Example 8

TLR-3 Signal Transport Pathway Regulated by the Compound of Formula 1

It is known that when toll-like receptor 3 (TLR-3) binds with dsRNA, TRIF then binds to TLR-3 transmitting the signal, which activates the pathway of NFkB, MAPK/AP-1, and IRF-3 and produces inflammatory cytokines. In this light, the following experiment was performed to confirm the effect of the compound of Formula 1 in the present invention on the signal transport pathway of TLR-3.

Figure 9A:
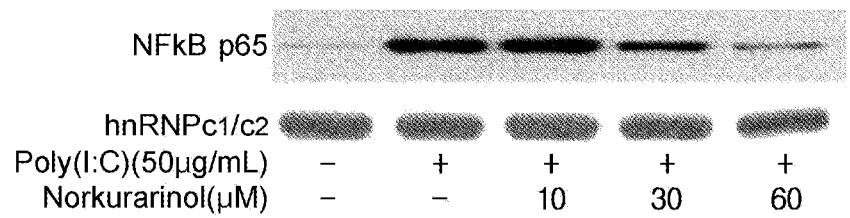
FIG. 9a shows the inhibitory effect of the compound of Formula 1 against the activity of NFκB P65 that moves to nucleus when activated by poly(I:C) treatment in THP-1 cells.
Figure 9B:
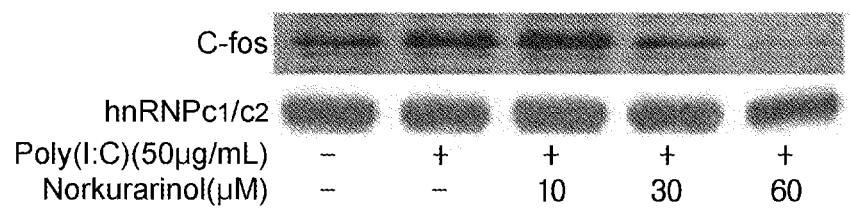
FIG. 9b shows the inhibitory effect of the compound of Formula 1 against the C-fos activity of AP-1 that moves to nucleus when activated by poly(I:C) treatment in THP-1 cells.
Figure 9C:
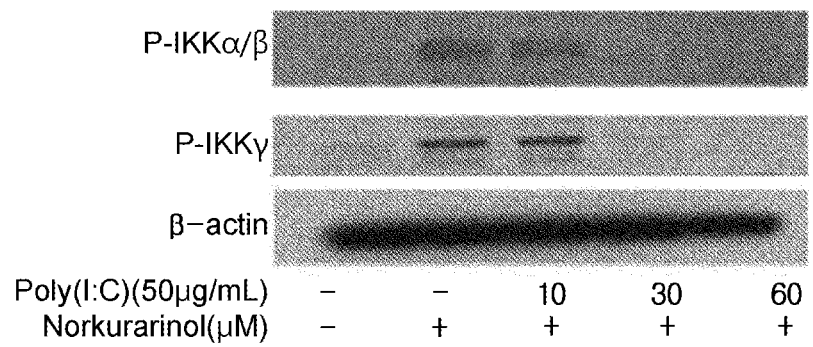
FIG. 9c shows the inhibitory effect of the compound of Formula against phosphorylation of IKK α/β and IKKγ which get phosphorylated by poly(I:C) treatment in THP-1 cells.
Figure 9D:
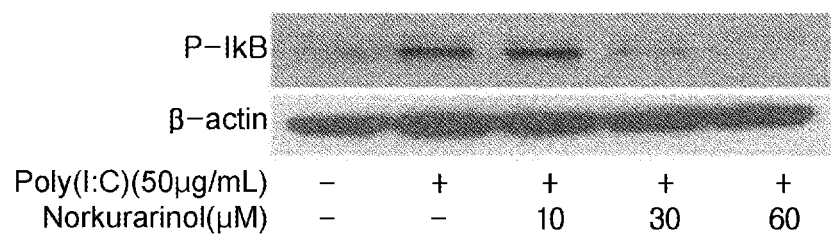
FIG. 9d shows the inhibitory effect of the compound of Formula 1 against phosphorylation of IκB which gets phosphorylated by poly(I:C) treatment in THP-1 cells.
Figure 9E:
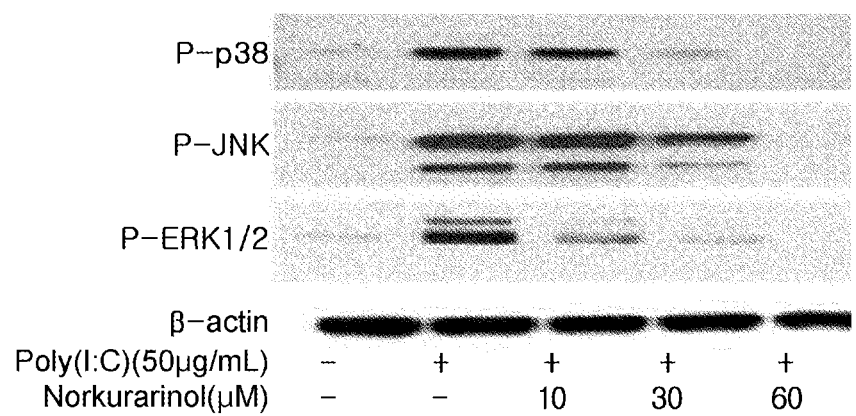
FIG. 9e shows the inhibitory effect of the compound of Formula 1 on phosphorylation of p38, JNK, and ERK1/2 which get phosphorylated by poly(I:C) treatment in THP-1 cells.

First, THP-1 cells were prepared at a density of $1.5\times10^6$ cells/well and cultured in culture medium RPMI 1640 which lacks FBS for 12 hours. Then, the cells were treated with the compound of Formula 1 at a concentration of 30 μM, 60 μM, and 100 μM 1 hour prior to the poly(I:C) treatment, and then treated with 50 μg/ml of poly (I:C) for 3 hours. After 3 hours of treatment, the cells were placed in a tube and pelleted down by centrifugation to remove cell media, washed with PBS once. Subsequently, the cells were added with NE-PER Nuclear extraction reagents (Thermo scientific) and cell lysis buffer to isolate nuclear extract and total protein extract which were then subject to western blot analysis. For the nuclear extract, the level of NFkB and c-Fos was monitored, and for the total protein extract, the level of MAPKs, IKK isoforms, and IRF3 was measured. As a result, it was found that the compound of Formula 1 reduced the transport of NFkB p65 and c-Fos to nucleus in a concentration-dependent manner (FIGS. 9a and 9b), and also reduced the phosphorylation of IKK and IkB which act before NFkB in the pathway in a concentration-dependent manner (FIGS. 9c and 9d). Furthermore, the phosphorylation of MAPKs, i.e., ERK, JNK, and p-38 which act before AP-1 activation in the pathway was reduced by the compound of Formula 1 in a concentration-dependent manner (FIG. 9e).

Example 9

Effect of S. flavescens Extract in Alleviation of the Symptoms of Rotavirus-Induced Porcine Diarrhea The specific pathogen-free pigs that are used as animal model was obtained by performing cesarean or hysterectomy in pigs in late pregnancy period that were bought from the certified pig breeding farm under National Agricultural Cooperative Federation. The type of virus used in this experiment was Korea strain G5P porcine serotype-A rotavirus, K85-A strain. First, a sample of rotavirus for inoculation was mixed with a certain concentration of crystal trypsin at a ratio of 1:9 (rotavirus:crystal trypsin) and placed in a 37° C. incubator for 30 minutes, then the MA-104 cells were inoculated with the rotavirus mixed with crystal trypsin and cultured at 37° C. for 1 hour. After 1 hour of culturing, a mixed solution of crystal trypsin and rotavirus was removed from the cell culture and replaced by a maintenance medium. Then if more than 80% of the cells showed cytopathic effect due to viral proliferation, the cells were subject to freezing-thawing three times, and a supernatant thereof was collected through centrifuging the cell culture and the supernatant was used in the inoculation experiment at a concentration of $5\times10^5$ fluorescence focus unit (FFU)/ml.

The specific pathogen-free pigs were divided into 3 test groups, i.e., 1) a negative control group without inoculation of virus, 2) a control group with inoculation of virus alone and no administration of a test compound, 3) a test group with inoculation of virus and administration of a test compound.

A sample of the methanol extract of S. flavescens to be examined for its activity was dissolved in 100% ethanol at various concentrations and then diluted with 0.9% saline solution. The prepared S. flavescens extract was orally administered in various doses the subject with diarrhea, and then manifestation of the diarrhea symptoms was monitored in comparison to a negative control group without inoculation of virus, and a positive control group inoculated with virus alone but without administration of the test compound. Furthermore, methanol extract of S. flavescens was mixed with steviocide and then administered in various doses. Subsequently, manifestation of the diarrhea symptoms was monitored in comparison to a negative control group without inoculation of virus, and a positive control group inoculated with virus alone but without administration of the test compound.

As a result, in a negative control group without inoculation of virus no clinical manifestation including diarrhea was observed. However, in a positive control group with inoculation of virus alone but without administration of the test compound, occurrence of severe diarrhea excreting mucus in stool was observed continuously 2 days after inoculation of virus. On the other hand, in the test group inoculated with virus and administered with 100 mg/ml and 200 mg/ml of S. flavescens extract at a volume of 1 ml four times a day each, the symptom of diarrhea was alleviated showing paste like stools instead of mucus, in comparison to the positive control group inoculated with virus only but without compound administration (FIG. 5a).

Example 10

Therapeutic Effect of S. flavescens Extract in the Treatment of Lesions of Digestive Organs Caused by Rotavirus Infection An autopsy was performed on the pigs obtained from Example 9 corresponding to the negative control group without inoculation of virus, the control group with inoculation of virus but no administration of a test compound, the test group with inoculation of virus and administration of a test compound. The collected tissues of small intestine were paraffin-embedded, sectioned, and stained with haemotoxylin and eosin. Then the dyed tissues were examined under optical microscope to monitor the morphological changes of intestinal mucosa.

As a result, there was no histological change observed in each of duodenum (FIG. 5b-A), duodenojejunal (FIG. 5b-B), and ileum (FIG. 5b-C) obtained from the specific pathogen-free pigs that were not inoculated with rotavirus. In contrast, the villus epithelial cells of duodenum (FIG. 5b-D), duodenojejunal (FIG. 5b-E), and ileum (FIG. 5b-F) were severely exfoliated in the control group with inoculation of virus but no administration of a test compound, which also showed manifestation of diarrhea caused by rotavirus. That is, atrophy and fusion of villi and an intense proliferation of crypts were observed in this histological study.

Figure 5B:
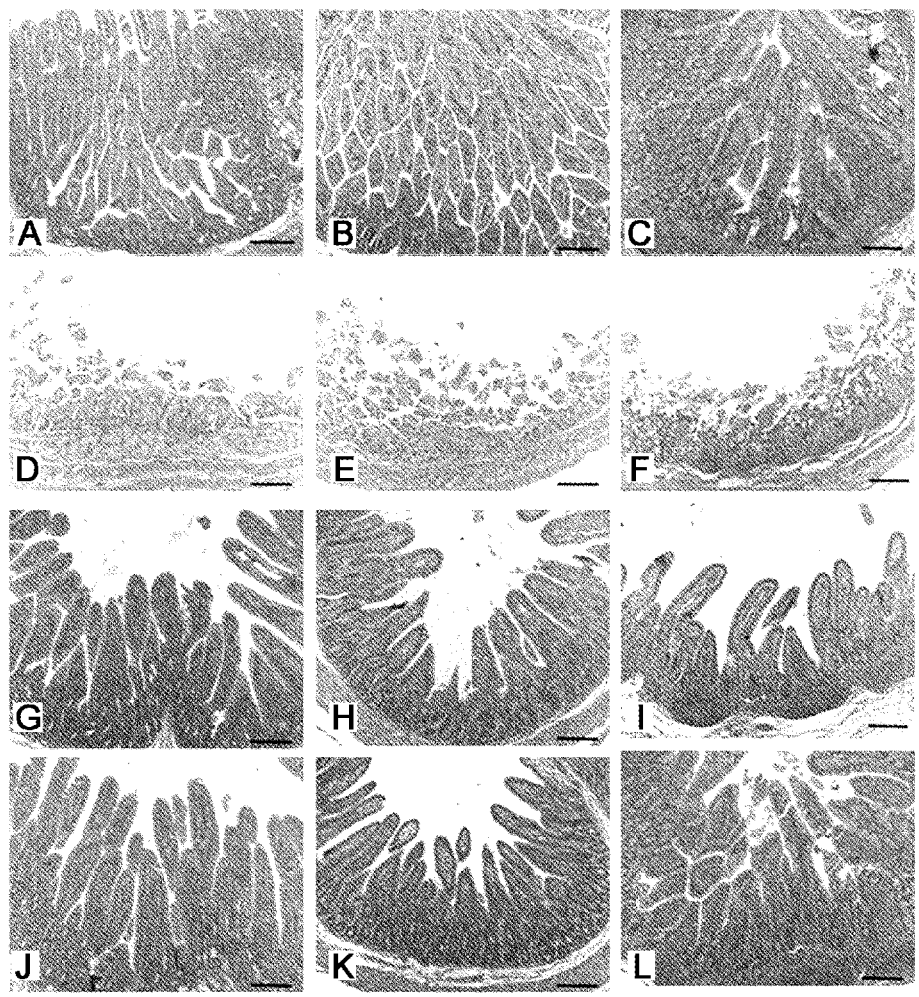
FIG. 5b shows the comparison of the histological changes in the lesion of digestive organ demonstrating the therapeutic effects of *S. flavescens* extract on the lesion development in digestive organ induced by rotavirus infection.

On the other hand, the results of histological study on each part of small intestine of the test group which was inoculated with rotavirus and administered with 100 mg/ml of S. flavescens extract at a volume of 1 ml four times a day demonstrated that exfoliation of villus epithelial cells, atrophy and fusion of villi and proliferation of crypts were alleviated in each of duodenum (FIG. 5b-G), duodenojejunal (FIG. 5b-H), and ileum (FIG. 5b-I), compared to the pigs inoculated with virus alone. Furthermore, when the concentration of S. flavescens extract administered was increased, that is the test group was inoculated with virus and administered with 200 mg/ml of S. flavescens extract at a volume of 1 ml four times a day, the histological study results showed that, similar to the group administered with 100 mg/ml of S. flavescens extract at a volume of 1 ml four times a day, exfoliation of villus epithelial cells, atrophy and fusion of villi and proliferation of crypts were alleviated in each of duodenum (FIG. 5b-J), duodenojejunal (FIG. 5b-K), and ileum (FIG. 5b-L), compared to the pigs inoculated with virus alone. These histological changes of small intestine in each test group are represented by an average of the villus/crypt ratio and degree of exfoliation of epithelial cell (FIG. 5c).

Example 11

Effect of the Co-Administration of S. flavescens Extract and Stevioside in Alleviation of the Porcine Diarrhea Caused by Rotavirus Infection As described in Example 9, the animal models were divided into three test groups, i.e., 1) a negative control group without inoculation of virus, 2) a control group with inoculation of virus alone and no administration of a test compound, 3) a test group with inoculation of virus and administration of a test compound. Unlike in Example 9, in this example, 100 mg/ml or 200 mg/ml of S. flavescens methanol extract was mixed with 3 g/ml of stevioside (prepared by dissolving 3 g of stevioside in 1 ml of 0.9% saline solution) and the mixed solution was administered to the subject, so that the effect of co-administration of two drugs can be determined.

As a result, it was found that when the biological material as a candidate antirotavirus substance was administered to a test group with inoculation of virus and administration of a test compound, it significantly alleviated the symptom of diarrhea in comparison to the pigs inoculated with virus alone (FIG. 6a). That is, the test group co-administered with 100 mg/ml of S. flavescens extract and 3 g/ml of stevioside showed the alleviation of diarrhea after 4 to 5 days of administration. Furthermore, when 200 mg/ml of S. flavescens extract and 3 μg/ml of stevioside were co-administered, the alleviation of diarrhea was observed after 1 day of administration at the earliest.

Example 12

Effect of the Co-Administration of S. flavescens Extract and Stevioside in Treatment of the Lesions of Digestive Organs Caused by Rotavirus Infection An autopsy was performed on the pigs obtained from Example 11 corresponding to the negative control group without inoculation of virus, the control group with inoculation of virus but no administration of a test compound, the test group with inoculation of virus and administration of a test compound. The collected tissues of small intestine were paraffin-embedded, sectioned, and stained with haemotoxylin and eosin. Then the dyed tissues were examined under optical microscope to monitor the morphological changes of intestinal mucosa as described in Example 10.

As a result, there was no histological change observed in each of duodenum (FIG. 6b-A), duodenojejunal (FIG. 6b-B), and ileum (FIG. 6b-C) obtained from the specific pathogen-free pigs that were not inoculated with rotavirus. In contrast, the villus epithelial cells of duodenum (FIG. 6b-D), duodenojejunal (FIG. 6b-E), and ileum (FIG. 6b-F) were severely exfoliated in the control group with inoculation of virus but no administration of a test compound, which also showed manifestation of diarrhea caused by rotavirus. That is, atrophy and fusion of villi and an intense proliferation of crypts were observed in this histological study.

On the other hand, the results of histological study on each part of small intestine of the test group which was inoculated with rotavirus and administered with 100 mg/ml of S. flavescens extract and 3 g/ml of stevioside four times a day demonstrated that exfoliation of villus epithelial cells, atrophy and fusion of villi and proliferation of crypts were alleviated in each of duodenum (FIG. 6b-G), duodenojejunal (FIG. 6b-H), and ileum (FIG. 6b-I), compared to the pigs inoculated with virus alone. Furthermore, when the test group was inoculated with virus and administered with 200 mg/ml of S. flavescens extract and 3 g/ml of stevioside four times a day, the histological study on each tissue sample showed that exfoliation of villus epithelial cells, atrophy and fusion of villi, and proliferation of crypts were alleviated in each of duodenum (FIG. 6b-J), duodenojejunal (FIG. 6b-K), and ileum (FIG. 6b-L), compared to the pigs inoculated with virus alone. These histological changes of small intestine in each test group are represented by an average of the villus/crypt ratio and degree of exfoliation of epithelial cell (FIG. 6c).

These results support that S. flavescens extract, fractions thereof, and compounds isolated therefrom represented by Formulas 1 to 8 of the present invention have therapeutic effects against diarrhea of animals and lesion of digestive organs by enhancing immunity through induction of the expression of interferon-β.

Example 13

Safety Test

The organ and tissue samples were obtained by performing an autopsy on the animal model of each test group, i.e., 1) the negative control group without inoculation of virus, 2) the control group with inoculation of virus but no administration of a test compound, 3) the test group with inoculation of virus and administration of a test compound. Then the organ and tissue samples were fixed with formalin, paraffin-embedded, sectioned to a thickness of 3 mm, and stained with haemotoxylin and eosin. Subsequently, the dyed samples were examined under optical microscope to monitor the morphological changes of the organs and tissues and test the safety of the administered drugs.

Preparation Example 1

Preparation of Powder

| | |
|---|---|
| Composition comprising S. flavescens extract, fractions thereof, or flavanone-type compound derived therefrom as an active ingredient | 0.1 g |
| Lactose | 1.5 g |
| Talc | 0.5 g |

The above compounds were mixed and filled in an airtight pack to prepare a powder formulation.

Preparation Example 2

Preparation of Tablet

| | |
|---|---|
| Composition comprising S. flavescens extract, fractions thereof, or flavanone-type compound derived therefrom as an active ingredient | 0.1 g |
| Lactose | 7.9 g |
| Crystalline Cellulose | 1.5 g |
| Magnesium stearate | 0.5 g |
| Total Weight | 10 g |

The above components were mixed and compressed into a tablet by a direct tableting method. Total weight of each tablet is 500 mg, in which the amount of active ingredient is 50 mg.

Preparation Example 3

Preparation of Capsule

| | |
|---|---|
| Composition comprising S. flavescens extract, fractions thereof, or flavanone-type compound derived therefrom as an active ingredient | 0.1 g |
| Corn starch | 5 g |
| Carboxy cellulose | 4.9 g |
| Total Weight | 10 g |

The above components were mixed and prepared into a powder form. The 500 mg of power was put into a hard capsule to prepare a capsule formulation.

Preparation Example 3

Preparation of Injectable Formulation

| | |
|---|---|
| Composition comprising S. flavescens extract, fractions thereof, or flavanone-type compound derived therefrom as an active ingredient | 0.1 g |
| Sterile distilled water for injection | suitable amount |
| pH adjusting agent | suitable amount |

The above formulation was prepared per 1 ampoule (2 ml) according to a conventional method for preparing injectable formulation.

Preparation Example 4

Preparation of Liquid Formulation

| | |
|---|---|
| Composition comprising S. flavescens extract, fractions thereof, or flavanone-type compound derived therefrom as an active ingredient | 0.1 g |
| Isomerized glucoses | 10 g |
| Mannitol | 5 g |
| Water | suitable amount |

The above components were dissolved in water according to a conventional method for preparing liquid formulation and 레몬향 was added in a suitable amount. Then the total volume of formulation was adjusted to 100 ml by adding more water, put in a brown bottle, and sterilized to prepare a liquid formulation.

What is claimed is:

1. A method for treating rotavirus-mediated diseases, comprising the step of administrating a composition to a rotavirus-infected subject, wherein the composition comprises any one of compounds of Formulas 1 to 8 or a pharmaceutically acceptable salt thereof in an amount of 100 mg or more per day as an active ingredient:

[Formula 1]

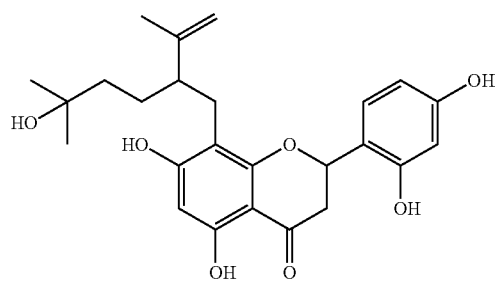

[Formula 2]

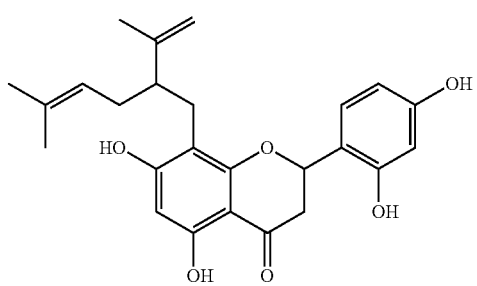

[Formula 3]

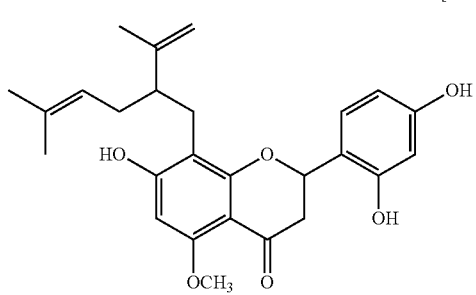

[Formula 4]

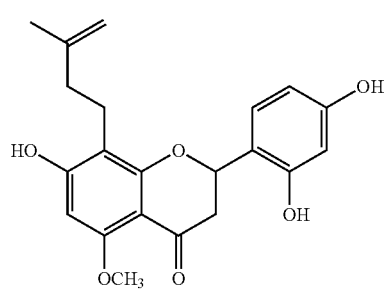

[Formula 5]

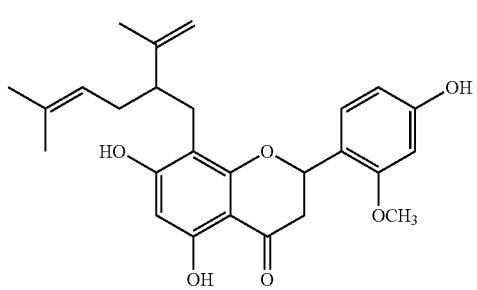

[Formula 6]

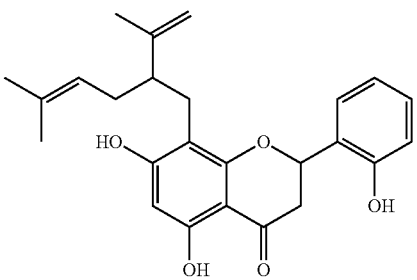

[Formula 7]

[Formula 8]

2. The method according to claim 1, wherein the composition further comprises *Stevia rebaudiana* extract or stevioside.

3. The method according to claim 1, wherein the composition is a feed additive, a pharmaceutical composition, or a food composition.

4. A method for treating rotavirus-mediated diseases, comprising the step of administrating a composition to a rotavirus-infected subject, wherein the composition comprises *Sophora flavescens* extract or fractions thereof comprising any one of compounds of Formulas 1 to 8 in an amount of 100 mg or more per day as an active ingredient.

5. The method according to claim 4, wherein the composition further comprises *Stevia rebaudiana* extract or stevioside.

6. The method according to claim 4, wherein the composition is a feed additive, a pharmaceutical composition, or a food composition.

* * * * *